(12) United States Patent
Deal et al.

(10) Patent No.: US 7,637,863 B2
(45) Date of Patent: Dec. 29, 2009

(54) WIRE GUIDE HOLDER

(75) Inventors: Stephen E. Deal, Charlotte, NC (US); David F. Waller, Winston-Salem, NC (US); Kenneth C. Kennedy, II, Clemmons, NC (US); Brian K. Rucker, King, NC (US); David M. Hardin, Winston-Salem, NC (US); John A. Karpiel, Winston-Salem, NC (US)

(73) Assignee: Wilson-Cook Medical Inc., Winston-Salem, NC (US)

( * ) Notice: Subject to any disclaimer, the term of this patent is extended or adjusted under 35 U.S.C. 154(b) by 786 days.

(21) Appl. No.: 10/903,679

(22) Filed: Jul. 29, 2004

(65) Prior Publication Data

US 2005/0090835 A1    Apr. 28, 2005

Related U.S. Application Data

(60) Provisional application No. 60/491,408, filed on Jul. 31, 2003, provisional application No. 60/563,968, filed on Apr. 21, 2004, provisional application No. 60/565,030, filed on Apr. 23, 2004, provisional application No. 60/570,656, filed on May 13, 2004, provisional application No. 60/571,142, filed on May 14, 2004.

(51) Int. Cl.
    *A61B 1/00*    (2006.01)
(52) U.S. Cl. .................. 600/104; 600/106; 604/164.04; 604/164.13

(58) Field of Classification Search .................. 600/102, 600/104, 106, 153, 154, 125, 107, 114, 113; 604/164.01–164.07, 164.13, 165.01–165.04
See application file for complete search history.

(56) References Cited

U.S. PATENT DOCUMENTS 1,251,778 A    1/1918    Humble (Continued)

FOREIGN PATENT DOCUMENTS

EP    0 510 851 A    10/1992

(Continued)

OTHER PUBLICATIONS

EPO Search Report dated Apr. 18, 2005.

(Continued)

*Primary Examiner*—John P Leubecker
*Assistant Examiner*—Victoria W Chen
(74) *Attorney, Agent, or Firm*—Brinks Hofer Gilson & Lione

(57) ABSTRACT

A wire guide holder having a body for securing an elongate medical wire or tube, such as a wire guide or catheter. The body is adapted to be attached to a scope or a bite block. The body can be provided with protrusions and/or grooves for holding a wire guide. The wire guide holder may be affixed to the medical scope by clamping. The wire guide holder can also be provided with a seal.

13 Claims, 21 Drawing Sheets

U.S. PATENT DOCUMENTS

| | | | |
|---|---|---|---|
| 4,000,739 A | 1/1977 | Stevens | |
| 4,143,853 A | 3/1979 | Abramson | |
| 4,198,959 A | 4/1980 | Otani | |
| 4,430,081 A | 2/1984 | Timmermans | |
| 4,610,665 A | 9/1986 | Matsumoto et al. | |
| 4,735,614 A | 4/1988 | Yapp et al. | |
| 4,844,092 A | 7/1989 | Rydell et al. | |
| 4,988,356 A | 1/1991 | Crittenden et al. | |
| 5,046,497 A | 9/1991 | Millar | |
| 5,125,905 A | 6/1992 | Wright et al. | |
| 5,159,861 A | 11/1992 | Anderson | |
| D333,182 S * | 2/1993 | Yoshikawa | D24/133 |
| 5,205,831 A | 4/1993 | Ryan | |
| 5,209,219 A * | 5/1993 | Hollobaugh | 600/154 |
| 5,281,203 A | 1/1994 | Ressemann | |
| 5,312,338 A | 5/1994 | Nelson et al. | |
| 5,323,768 A | 6/1994 | Saito et al. | |
| 5,325,746 A | 7/1994 | Anderson | |
| 5,325,868 A | 7/1994 | Kimmelstiel | |
| 5,338,314 A | 8/1994 | Ryan | |
| 5,342,292 A | 8/1994 | Nita et al. | |
| 5,423,331 A | 6/1995 | Wysham | |
| 5,443,078 A | 8/1995 | Uflacker | |
| 5,453,097 A | 9/1995 | Paradis | |
| 5,513,633 A | 5/1996 | Islava | |
| 5,575,771 A | 11/1996 | Walinsky | |
| 5,579,779 A | 12/1996 | Humphrey | |
| 5,579,780 A | 12/1996 | Zadini et al. | |
| 5,658,309 A | 8/1997 | Berthiaume et al. | |
| 5,730,150 A | 3/1998 | Peppel et al. | |
| 5,762,070 A | 6/1998 | Nagamatsu | |
| 5,769,786 A | 6/1998 | Wiegel | |
| 5,810,781 A | 9/1998 | Bierman | |
| 6,059,484 A | 5/2000 | Greive | |
| 6,096,009 A * | 8/2000 | Windheuser et al. | 604/165.01 |
| 6,117,070 A * | 9/2000 | Akiba | 600/154 |
| 6,126,633 A | 10/2000 | Kaji et al. | |
| 6,134,754 A | 10/2000 | Lampropoulos et al. | |
| 6,280,432 B1 | 8/2001 | Turovskiy et al. | |
| 6,289,661 B1 * | 9/2001 | Boland | 57/58.63 |
| 6,312,404 B1 | 11/2001 | Agro et al. | |
| 6,346,093 B1 | 2/2002 | Allman et al. | |
| 6,450,976 B2 | 9/2002 | Korotko et al. | |
| 6,517,518 B2 * | 2/2003 | Nash et al. | 604/164.02 |
| 6,520,951 B1 | 2/2003 | Carrillo et al. | |
| 6,533,782 B2 | 3/2003 | Howell et al. | |
| 6,551,273 B1 * | 4/2003 | Olson et al. | 604/103.03 |
| 6,595,982 B2 | 7/2003 | Sekino et al. | |
| 6,602,240 B2 * | 8/2003 | Hermann et al. | 604/500 |
| 6,663,597 B1 | 12/2003 | Windheuser et al. | |
| 6,679,872 B2 * | 1/2004 | Turovskiy et al. | 604/513 |
| 6,746,466 B2 | 6/2004 | Eidenschink | |
| 6,827,683 B2 * | 12/2004 | Otawara | 600/123 |
| 6,827,718 B2 | 12/2004 | Hutchins et al. | |
| 6,893,393 B2 * | 5/2005 | Carrillo | 600/154 |
| 7,198,599 B2 * | 4/2007 | Goto et al. | 600/154 |
| 2002/0007152 A1 * | 1/2002 | Hermann et al. | 604/167.04 |
| 2002/0087100 A1 | 7/2002 | Onuki et al. | |
| 2002/0177869 A1 * | 11/2002 | Eidenschink et al. | 606/194 |
| 2003/0088153 A1 | 5/2003 | Carrillo et al. | |
| 2003/0233043 A1 * | 12/2003 | Windheuser et al. | 600/434 |
| 2004/0015050 A1 * | 1/2004 | Goto et al. | 600/104 |
| 2004/0030290 A1 * | 2/2004 | Mangano et al. | 604/164.04 |
| 2004/0049095 A1 * | 3/2004 | Goto et al. | 600/107 |
| 2004/0106852 A1 * | 6/2004 | Windheuser et al. | 600/125 |
| 2004/0162465 A1 * | 8/2004 | Carrillo | 600/104 |
| 2004/0199197 A1 | 10/2004 | Eidenschink et al. | |
| 2005/0121028 A1 | 6/2005 | Scopton | |

FOREIGN PATENT DOCUMENTS

| | | |
|---|---|---|
| EP | 0 335 581 B1 | 8/1993 |
| WO | PCT/JP99/01346 | 3/1999 |
| WO | WO 99/47202 A | 9/1999 |
| WO | WO 01/49363 A | 7/2001 |
| WO | WO 02/094365 A | 11/2002 |
| WO | WO 2005/072807 A | 8/2005 |

OTHER PUBLICATIONS

Pursuant to MPEP §2001.06(b), U.S. Appl. No. 60/491,408, filed Jul. 31, 2003 is co-pending and relates to "Wire Guide Holder".

Pursuant to MPEP §2001.06(b), U.S. Appl. No. 60/563,968, filed Apr. 21, 2004 is co-pending and relates to "Wire Guide Holder".

Pursuant to MPEP §2001.06(b), U.S. Appl. No. 60/565,030, filed Apr. 23, 2004 is co-pending and relates to "Wire Guide Holder".

Pursuant to MPEP §2001.06(b), U.S. Appl. No. 60/570,656, filed May 13, 2004 is co-pending and relates to "Wire Guide Holder".

Pursuant to MPEP §2001.06(b), U.S. Appl. No. 60/571,142, filed May 14, 2004 is co-pending and relates to "Wire Guide Holder".

International Search Report from corresponding PCT application No. PCT/US2006/003940, dated Jul. 19, 2007, 8 pages.

* cited by examiner

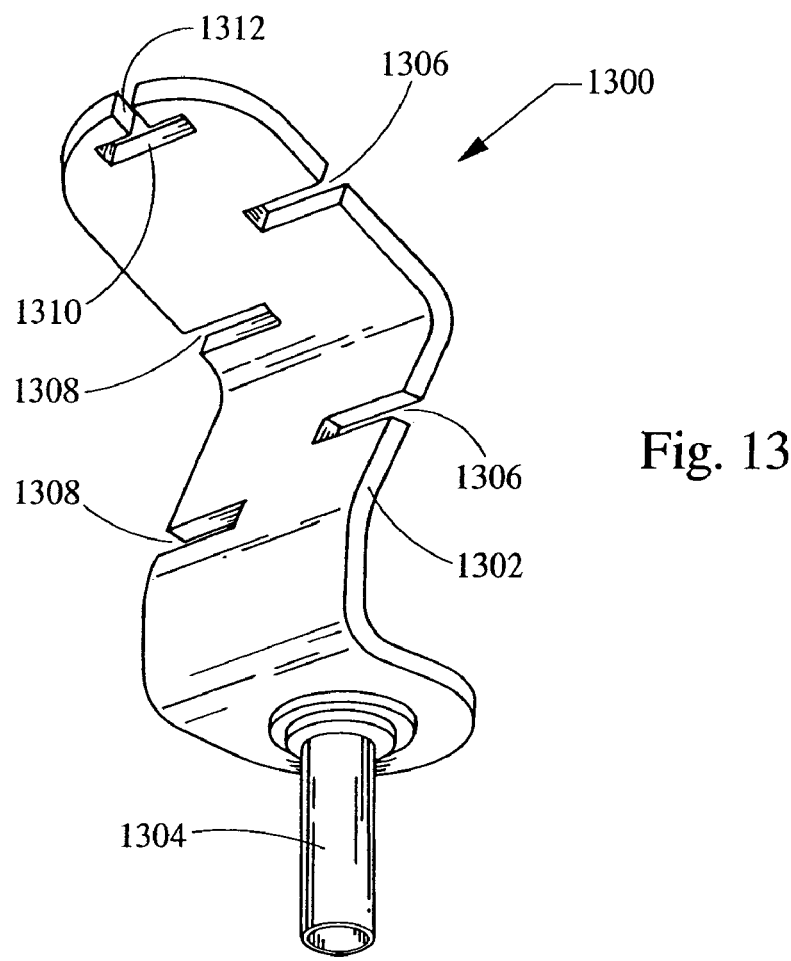
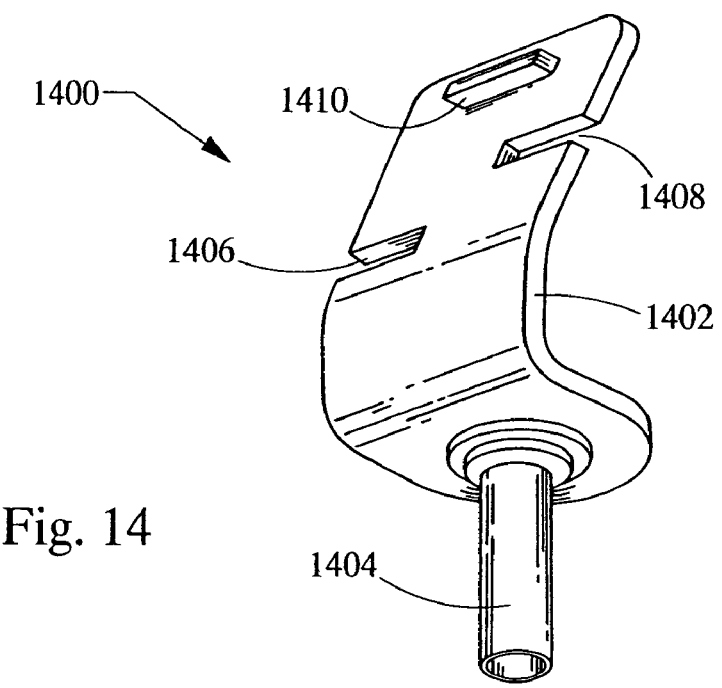
Fig. 13
Fig. 14

WIRE GUIDE HOLDER

RELATED APPLICATIONS

This application is a non-provisional application related to Ser. No. 60/491,408, filed Jul. 31, 2003, Ser. No. 60/563,968, filed Apr. 21, 2004, Ser. No. 60/565,030, filed Apr. 23, 2004, Ser. No. 60/570,656, filed May 13, 2004, and Ser. No. 60/571,142, filed May 14, 2004.

BACKGROUND OF THE INVENTION

The invention is useful in the area of medical procedures, particularly medical procedures involving an introducer catheter, a wire guide, an endoscope, or the like.

Endoscopes are routinely used to perform various medical procedures in areas of the body that are difficult to visualize, access, or that may otherwise require an open procedure to access. Further, in many cases, endoscopes allow visual access to a target anatomy without the use of radioactive fluoroscopy. Endoscopes also provide a working channel for other devices to be passed through the endoscope and directly target an internal body lumen or area of the anatomy. For example, catheters, wire guides and other types of elongated medical devices are frequently passed through the working channel of an endoscope to perform a diagnostic or medical procedure at a location near the distal end of the endoscope.

Wire guides are used during many procedures in the gastrointestinal system, including the pancreatobiliary system (i.e., the biliary tree), the stomach, and the esophagus. Wire guides are long, slender, relatively flexible wires that are used to gain and maintain access to the body's narrow passageways during minimally invasive medical procedures. Because of the substantial length of wire guides, they can be cumbersome and require constant, delicate manipulation by a physician.

Wire guides often must be maintained in a stationary position relative to the patient while a physician performs various procedures. In particular, maintaining the wire guide in a stationary position is important to prevent loss of access to a target anatomy, for example, a duct in the biliary tree. Also, during an esophageal dilation, a physician must secure a wire guide within the esophagus and across an esophageal stricture as one or more dilators are advanced over the wire guide. Likewise, during a percutaneous endoscopic gastrostomy (PEG) tube placement, a wire guide must be secured relative to the patient's mouth, esophagus, and stomach as a physician inserts a feeding tube.

Due to the complexity of these procedures, physicians often need the assistance of another person to hold the endoscope, manipulate the catheter, and/or hold the wire guide. However, this shifts the focus of the assistant from their other areas of responsibility, such as checking the patient, checking monitors for relevant information, or carrying out other tasks.

As a way of simplify procedures involving wire guides, wire guide locking devices have been developed to lock a wire guide in a stationary position. Available locking devices utilize a wedge or V-shaped slot having gap that narrows to a width that is narrower than the width of the wire guide. The wire guide is locked into the device by jamming or wedging it into the wedge or V-shaped slot.

Such prior art devices, however, have a multitude of significant drawbacks. One drawback is that the wire guide is often damaged by available wire locking devices. Specifically, the act of jamming or wedging a wire guide into the locking slot can damage or strip the wire guide, thereby rendering wire guide unfit for use. This is because a concentrated wedging force that is sufficient to seat the wire guide into the locking slot must be applied to the wire guide at a location adjacent to the locking slot. Such a force can easily kink, strip, or deform the wire guide. In addition, it is difficult to determine if the wire guide has been properly seated and locked in the locking slot. As a consequence, the physician may pull of the wire guide to "test" whether it will move relative to the device, which may further damage or strip the wire guide.

Another drawback is that previously available locking devices utilize a small, J-shaped slot to access the wedge portion of the locking device. As a result, a physician must maneuver the wire guide in and out of the J-shaped slot. However, maneuvering the wire guide is time-consuming and distracting to the physician, and is difficult to perform quickly, effectively, and efficiently during complicated medical procedures. Moreover, this maneuvering requires that a physician look for the J-shaped slot and visually confirm that the wire guide is properly engaged.

BRIEF SUMMARY OF THE INVENTION

Accordingly, it is an object of the present invention to provide a medical device having features that resolve or improve upon one or more of the above-described drawbacks.

According to a first aspect of the present invention, the foregoing object is obtained by providing a wire guide holder having a seal and a body. The seal is adapted to receive a wire guide, and the body is attached to the seal and is adapted to be attached to an elongate medical tube. The elongate medical tube may include an endoscope. The endoscope may have an access port and an insert, and the body may be affixed to the access port. The body may also be affixed to an insert, insert groove, or insert rim. The body may be snap-fit together.

Another embodiment of the present invention includes a wire guide holder having a body and a wire holder with at least three extensions for holding a wire guide. The body may be attached to a medical tube such as, for example, an endoscope. The extensions may include grooves and may be of varying size. The wire guide may be threaded between the extensions.

Another embodiment of the present invention includes a system for holding a wire guide including an endoscope, having an access port and an insert, and a wire guide holder. The wire guide holder may be affixed to the insert/access port by clamping. The wire guide holder may also be affixed to a rim or groove of the insert.

Another embodiment of the present invention includes a bite block and a wire guide holder attached to the bite block. The wire guide holder has a body and a wire holder with at least three extensions for holding a wire guide. The wire guide holder can be formed integrally with the bite block or can be rotatably attached to the bite block.

BRIEF DESCRIPTION OF SEVERAL VIEWS OF THE DRAWINGS

Embodiments of the present invention will now be described by way of example with reference to the accompanying drawings, in which:

FIG. 13 illustrates an exemplary wire guide holder;

FIG. 14 illustrates an exemplary wire guide holder;

DETAILED DESCRIPTION

Figure 1:
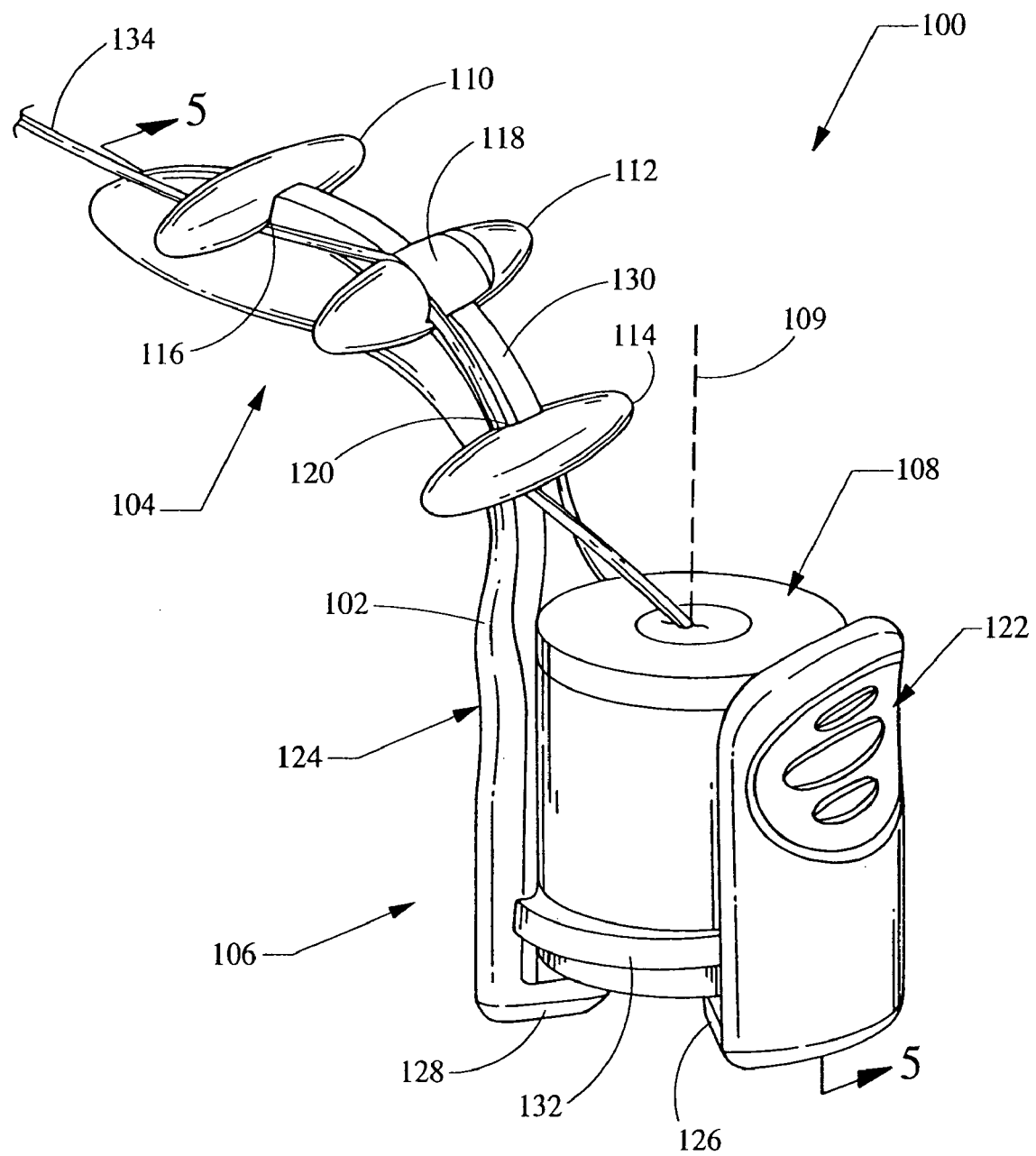
FIG. 1 illustrates an exemplary wire guide holder.

The invention is described with reference to the drawings in which like elements are referred to by like numerals. The relationship and functioning of the various elements of this invention are better understood by the following detailed description. However, the embodiments of this invention as described below are by way of example only, and the invention is not limited to the embodiments illustrated in the drawings. It should also be understood that the drawings are not to scale and in certain instances details have been omitted, which are not necessary for an understanding of the present invention, such as conventional details of fabrication and assembly.

In general, FIG. 1 illustrates a wire guide holder 100 having a holder body 102, a wire holder 104, and a seal holder 106 enclosing a seal 108. In addition, the wire holder 104 has three spaced apart posts 110, 112, 114, each of which extend generally perpendicularly from a central spine 130. Posts 110, 112, 114, each include one or more guide grooves 116, 118, 120, respectively. More specifically, posts 110 and 114 each include a guide groove, 116 and 120, respectively, on each side of the central spine 130, whereas post 112 includes a single, relatively large guide groove 118 that extends past the sides of the central spine 130. As will be explained below, the guide grooves 116, 118, 120 each define an open gap having a width that is greater than the width of a typical wire guide or elongate medical device 134. The central spine 130 of the wire holder 104 in this embodiment extends and curves away from the central or vertical axis 109 formed by the seal 108.

The seal holder 106 includes opposing finger presses 122, 124, which are flexibly attached to each other by bridge member 132. The finger presses 122, 124 are ergonomically configured for receiving, by way of example, the thumb and forefinger of a user. Squeezing finger presses 122 and 124 together causes clamps 126 and 128 to open, i.e., to spread apart. Conversely, releasing the finger presses causes clamps 126 and 128 to close, i.e., to move together. One or more distinct forces cause clamps 126 and 128 to clamp down onto an endoscope. First, seal holder 106 creates a return force, as it tends toward its natural, closed state. Second, seal 108 provides a return force when it is squeezed by the physician applying pressure to finger presses 122 and 124. As will be explained below, clamps 126, 128, combined with the return force created by seal 108 permit the wire guide holder 100 to be clamped onto an endoscope or similar device.

Wire holder 104 is configured to receive and hold a wire guide, catheter, or similar type of elongate medical device (hereinafter collectively referred to as a "wire guide"). When the wire guide holder 100 is attached to an endoscope (see FIGS. 2 and 3), a wire guide 134 extending through the working channel of the endoscope would extend out through the seal 108 (see FIG. 1). While in this position, the wire guide 134 can be weaved around securing posts 110, 112, 114, and positioned in guide grooves 116, 118, 120. Guide grooves 116, 118, 120 prevent the wire guide 134 from slipping off securing posts 110, 112, and 114.

When the wire guide 134 is weaved around the securing posts 110, 112, 114, the wire guide 134 is restricted against longitudinal movement. This is because the stiffness or resistance to bending of a typical wire guide results in a lateral force that is applied to the sides of the posts 110, 112, 114. This lateral force generates a frictional force between the side of the wire guide 134 and the side of each of the posts 110, 112, 114 that is sufficient to inhibit, limit, or to some extent prevent the longitudinal movement of the wire guide 134. However, the wire guide 134 is not damaged by the wire guide holder 100 since the wire guide 134 is not pinched between opposing surfaces of the wire guide holder 100, and because the lateral forces applied to the wire guide 134 are spread across several locations. In particular, this configuration avoids damage to the wire guide, such as stripping, which can result from locking it within a wedge or v-shaped slot as in prior art devices.

Optionally, friction pads can be added to guide grooves 116, 118, 120. These friction pads further prevent a wire guide from slipping off securing posts 110, 112, 114. Moreover, such friction pads can further limit the longitudinal sliding or movement of an elongate medical device that is engaged by the wire guide holder. Friction pads can be formed of compliant or tacky materials, for example, rubber.

Figure 2:
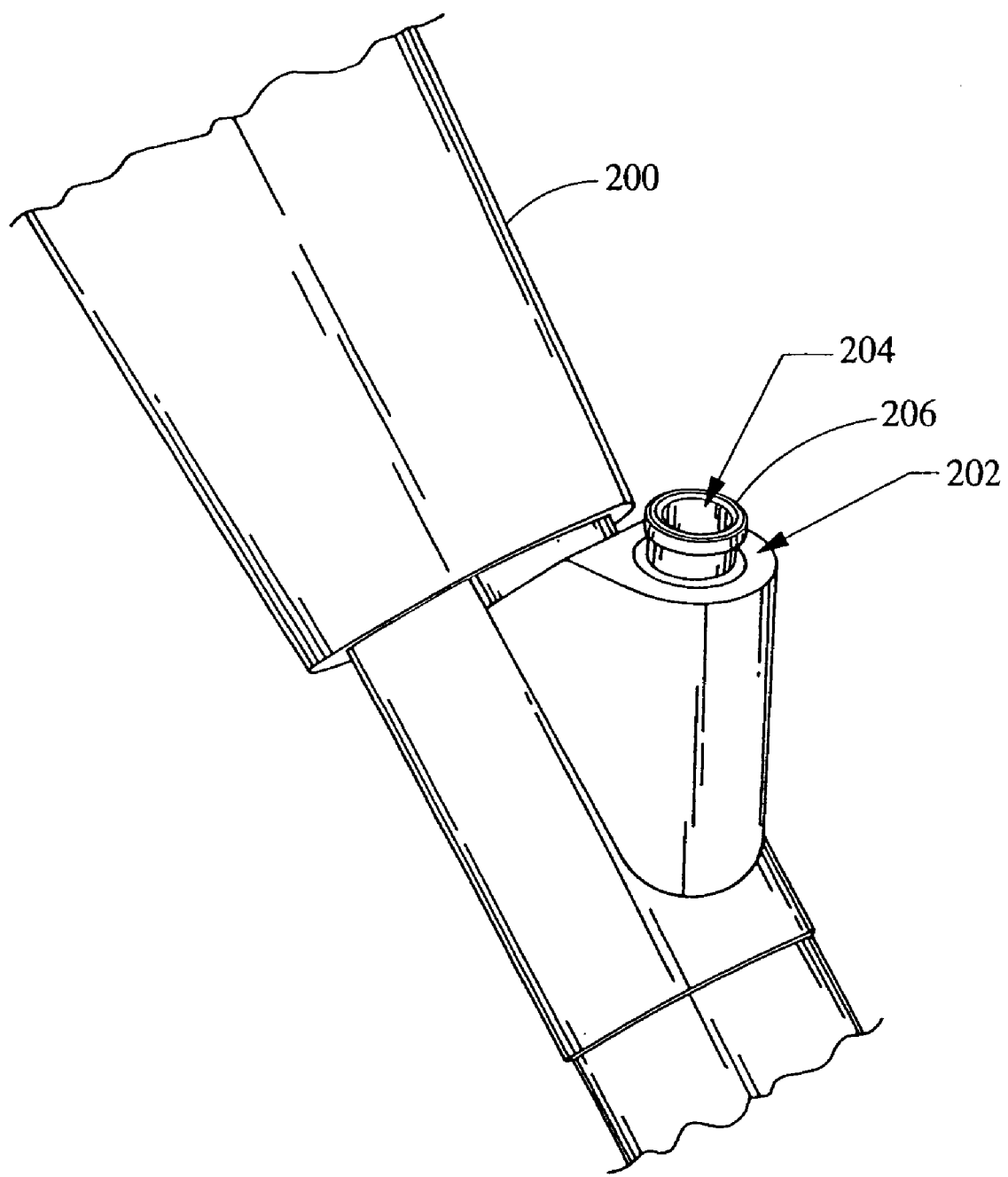
FIG. 2 illustrates an exemplary endoscope and endoscope access port.
Figure 3:
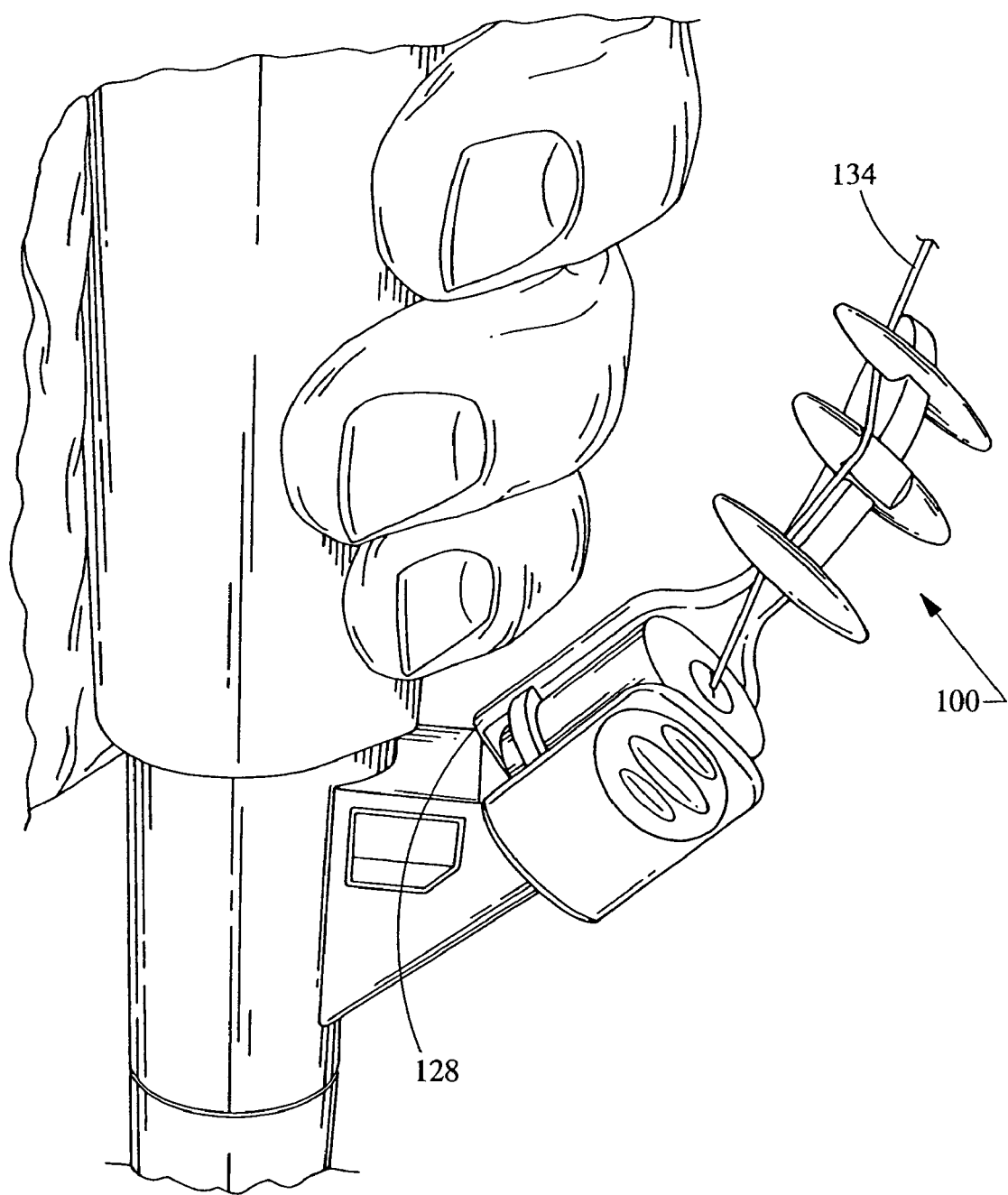
FIG. 3 illustrates an exemplary wire guide holder affixed to an endoscope.

FIG. 2 illustrates an exemplary endoscope 200 and a metal insert 202 leading into an access port 204 of the endoscope 200. The access port 204 provides access to a working channel (not shown) that extends distally through the interior of the endoscope 200. The metal insert 202 has a lip 206 and may be covered by an access port cover (not shown), which may be removed to access the access port 204 and the metal insert 202. FIG. 3 illustrates the wire guide holder 100 (illustrated in FIG. 1) clamped or otherwise attached to the endoscope 200

(illustrated in FIG. 2). In particular, clamps 126, 128 of the wire guide holder 100 are configured to engage the lip 206 of a metal insert 204 of endoscope 200. The wire guide holder 100 is attached or removed from the endoscope 200 by pressing finger presses 122 and 124 together so as to cause clamps 126 and 128 to open and disengage from lip 206.

Figure 4:
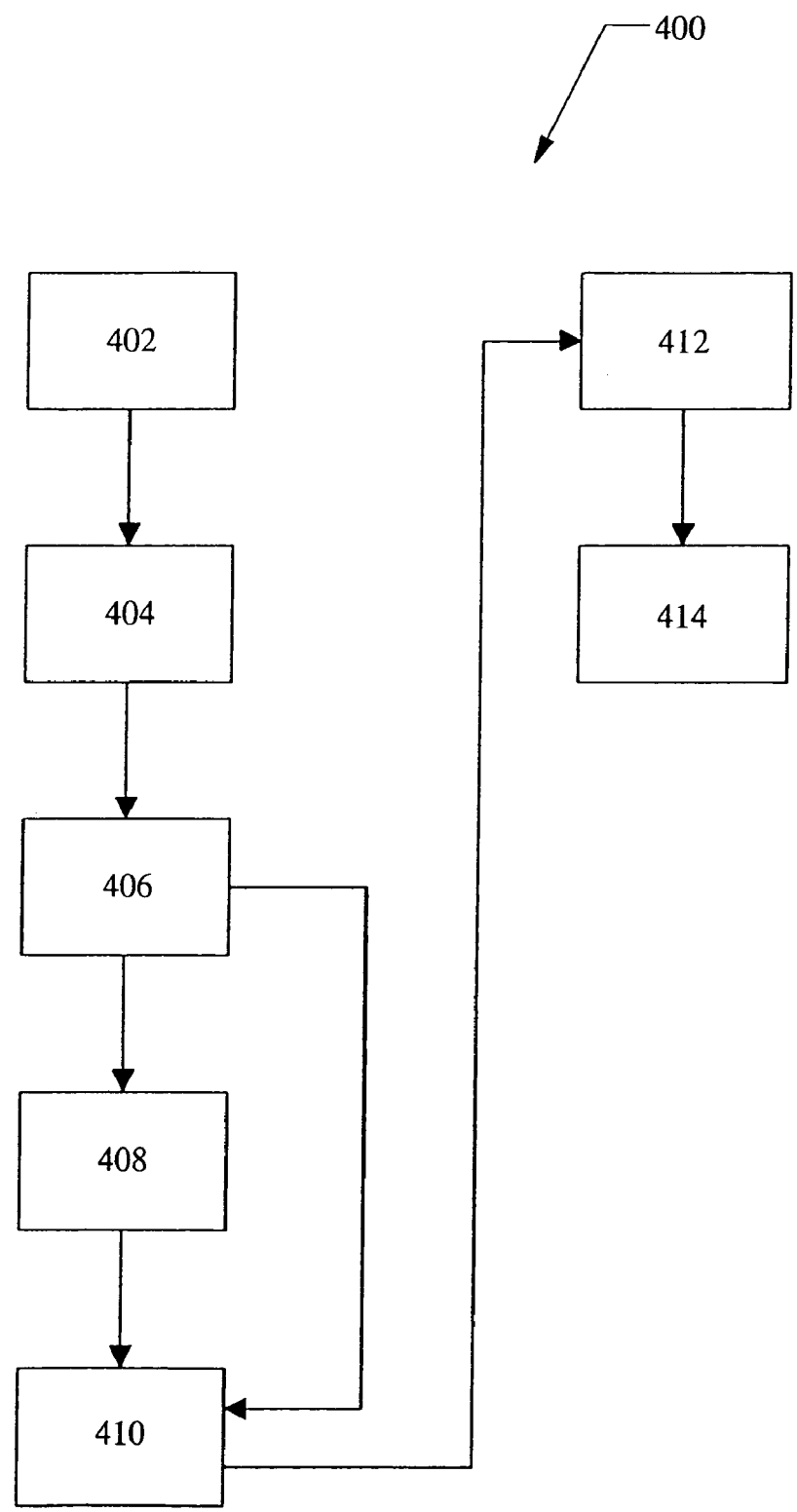
FIG. 4 illustrates a method for use of an exemplary wire guide holder.

FIG. 4 illustrates a flow chart 400 of method steps for use of an exemplary wire guide holder in endoscopic procedures, particularly a cannulation followed by a sphincterotomy. In this particular exemplary method, the use of a intraductal exchange biliary cannulation catheter, a intraductal exchange sphincterotome catheter, and a intraductal exchange length wire guide is described. Nevertheless, it should be understood that a variety of elongate members (e.g., wire guides and catheters, among others) can be used with the exemplary wire guide holder. This includes elongate members for biliary or non-biliary applications. Indeed, the exemplary wire guide holder can be used in conjunction with a variety of systems, including rapid exchange, monorail, or over-the-wire, peel away and/or non-peel away systems.

A physician can perform an intraducatal exchange as follows. Initially, in step 402, a physician can prepare an intraductal exchange biliary cannulation catheter by advancing the distal end of a wire guide into the intraducatal exchange port and out of the distal end port of the catheter. Step 404 involves inserting the wire guide and catheter through a seal in the wire guide holder, through the access port of the endoscope, and into the endoscope working channel. After readying the wire guide and cannulation catheter to cannulate the papilla of vater, the papilla is cannulated in step 406. After cannulation, the wire guide and cannulating catheter are advanced into the bile duct. At this point, step 408 is performed by securing one of the wire guide and the catheter in the wire guide holder. For example, the wire guide can be weaved through spaced apart posts, as shown in FIG. 1, thereby securing the wire guide relative to the catheter and endoscope. At this point, advancing the catheter relative to the wire guide disconnects the wire guide and catheter. Once the wire guide and catheter are disconnected, since the wire guide is secured by the wire guide holder, the physician can continue to use the catheter without inadvertently moving the wire guide and losing access to the target anatomy. Additionally, because the wire holder directs proximal end of the wire guide laterally, as shown in FIG. 1, the physician can easily position the wire guide so that it is not in the physicians way.

Subsequently, in step 410, with the wire guide still secured by the wire holder portion of the wire guide holder, the catheter can simultaneously be secured in the same fashion by the same wire guide holder to limit movement of the catheter. Then, in step 412, the catheter can be released from the wire guide holder and removed altogether. In step 414, the wire guide is released from the wire holder portion of the wire guide holder.

Figure 5:
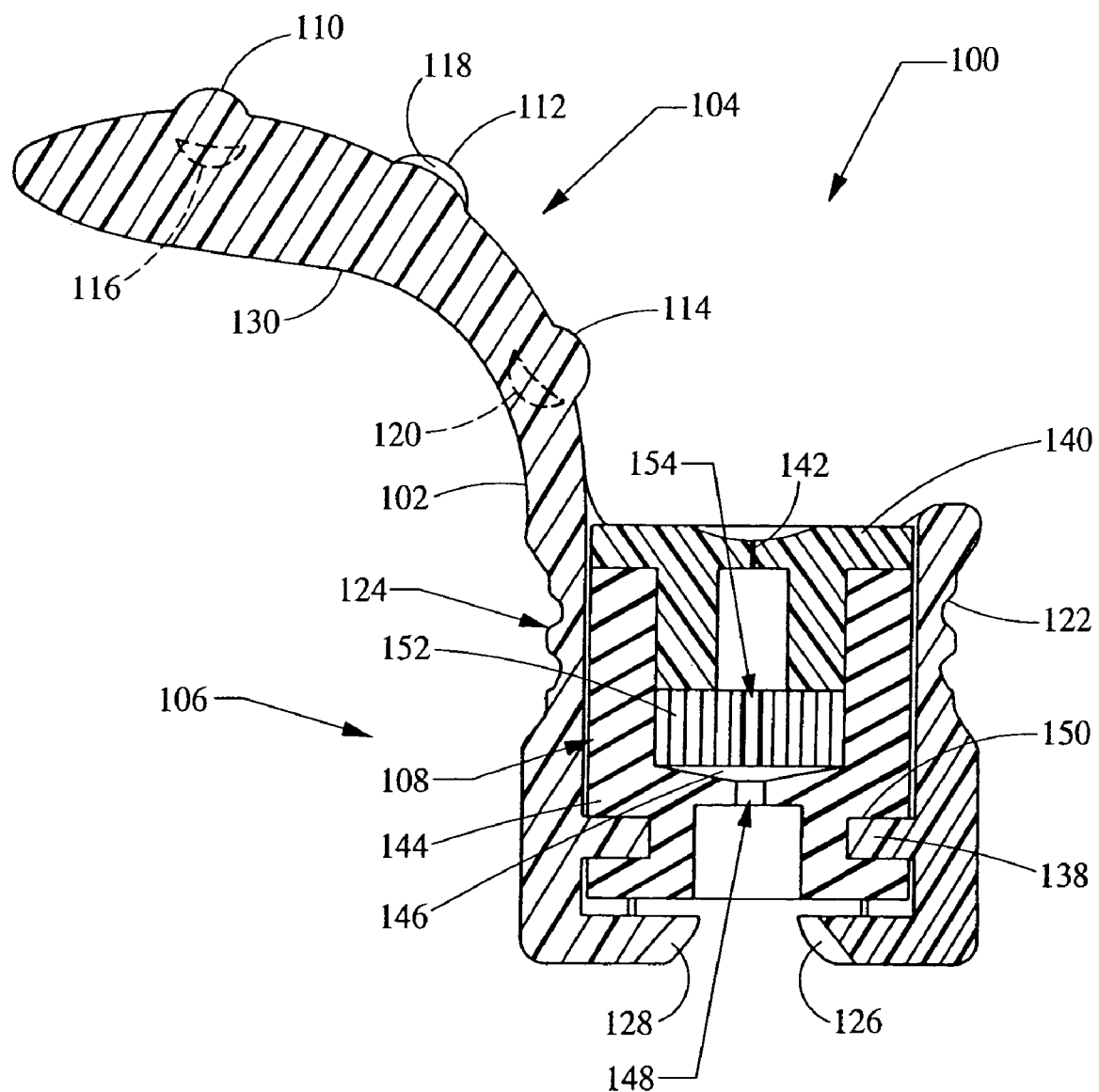
FIG. 5 illustrates a cut away view of an exemplary wire guide holder.

FIG. 5 illustrates a cut away view of the exemplary wire guide holder 100. As explained above, the wire guide holder 100 has a seal holder 106 for supporting a seal 108. In the embodiment illustrated, seal 108 is a multi-part or composite seal comprising a proximal seal 140 with a slit 142 and a distal seal 144 with a conical portion 146 leading to a hole 148.

The distal seal 144 also has a notch 150 that receives the seal holder 138 projecting inwardly from the interior surface of the seal holder 106. This notch 150 allows the seal 108 to be secured to the wire guide holder 100. In one exemplary embodiment, the seal holder 106 is snap-fit around the seal 108 to secure the seal 108 in place. An inner foam disc 152 is secured between the proximal seal 104 and the distal seal 144. The foam disc 152 may have a slit 154 or an opening of some other shaped cut into or through it.

Proximal seal 140, distal seal 146, and foam disk 152 are each configured to allow one or more wire guides, catheters, or similar elongate devices extending out of the port 204 of the endoscope 200 (see FIG. 2) to pass there through while maintaining an adequate seal there about. In other words, each of these seals limits the escape of any fluids that may be present within the working channel of the endoscope without inhibiting the insertion or movement of wire guides, catheters, or similar elongate devices. This configuration can be of particular benefit in preventing bodily fluids such as bile and blood from escaping and contaminating the physician and the working environment. The design and configuration of each of these seals, including the types of materials from which they are manufactured, are well known to those skilled in the art. Although the exemplary seal 108 displays a hole 148, a slit 142, and a slit 154, other types of slits, torn holes, arranged slits, or penetrable seals may alternatively be used. For example, other seal configurations include duckbill, membrane with slit (e.g., polystyrene, silicone, or another compliant polymer material), foam seal with small central aperture (e.g., silicon, polyurethane, etc.), or other designs having the ability to seal around the catheter and wire guide to prevent any proximally migrating fluid from exiting the channel.

In the embodiment illustrated in FIG. 5, the distal seal 146 is spaced a short distance away from the upper surface of clamps 126, 128. This provides a gap or open space for the lip 206 of the endoscope 200 (see FIG. 2). Nevertheless, the lower surface of the distal seal 146 is configured to elastically press against and form at least a partial fluid seal with the metal insert 202 (and access port 204) of endoscope 200 when the wire guide holder 100 is attached thereto.

Figure 6:
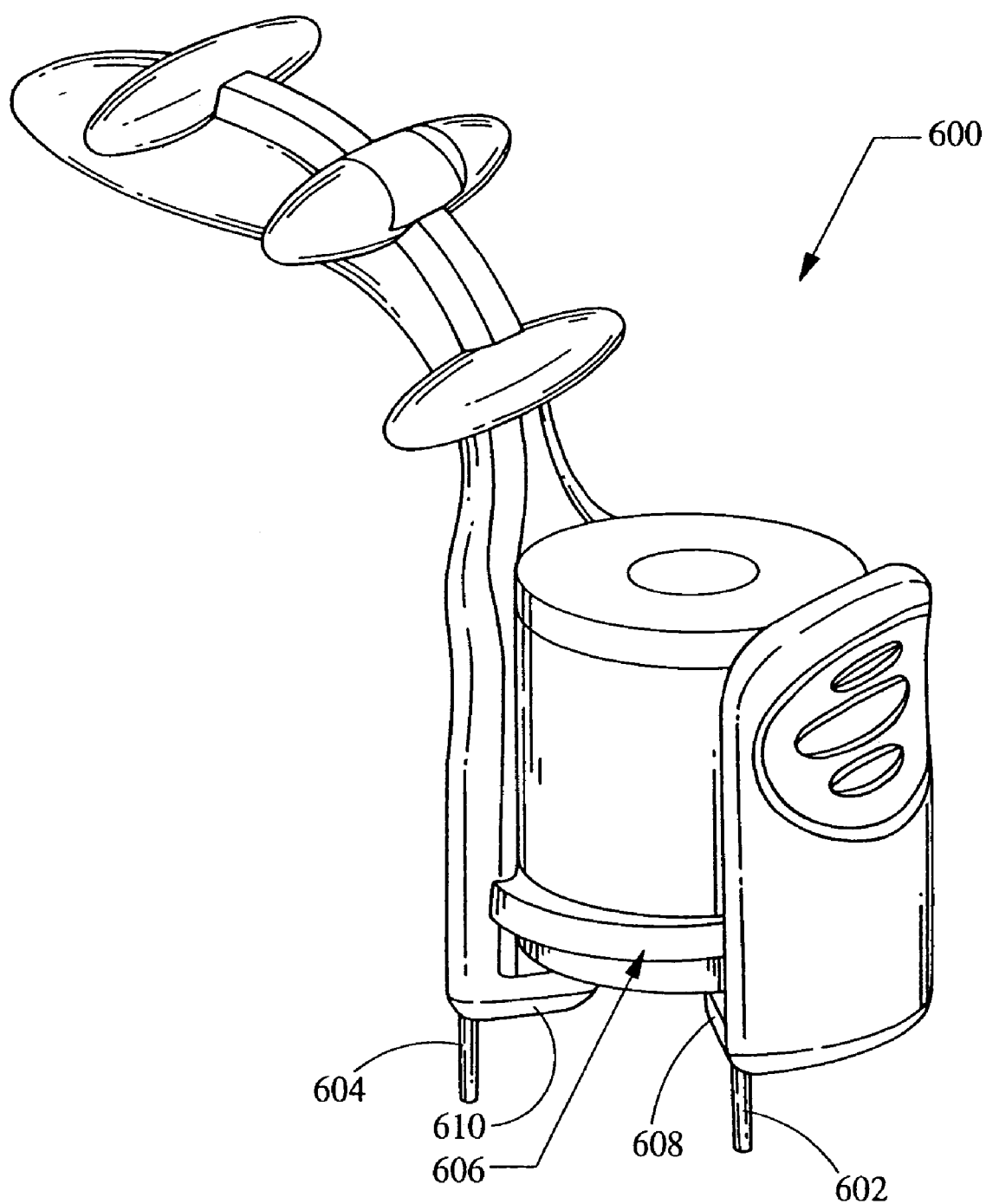
FIG. 6 illustrates an exemplary wire guide holder having stabilizing pegs.

FIG. 6 illustrates another exemplary embodiment of a wire guide holder 600. This wire guide holder 600 is similar to the wire guide holder 100 illustrated in FIG. 1. However, the wire guide holder 600 of FIG. 6 has two alignment pins or movement restrictors 602, 604 that project or extend outwardly from the lower surface of wire guide holder 600. When the wire guide holder 600 is attached to endoscope 200 (see FIG. 2), the movement restrictors 602, 604 extend along side of the access port 204 and engage surface features thereof (not shown). More specifically, the movement restrictors 602, 604 limit wire guide holder 600 from rotating relative to the access port 204 of the endoscope 200.

Figure 7:
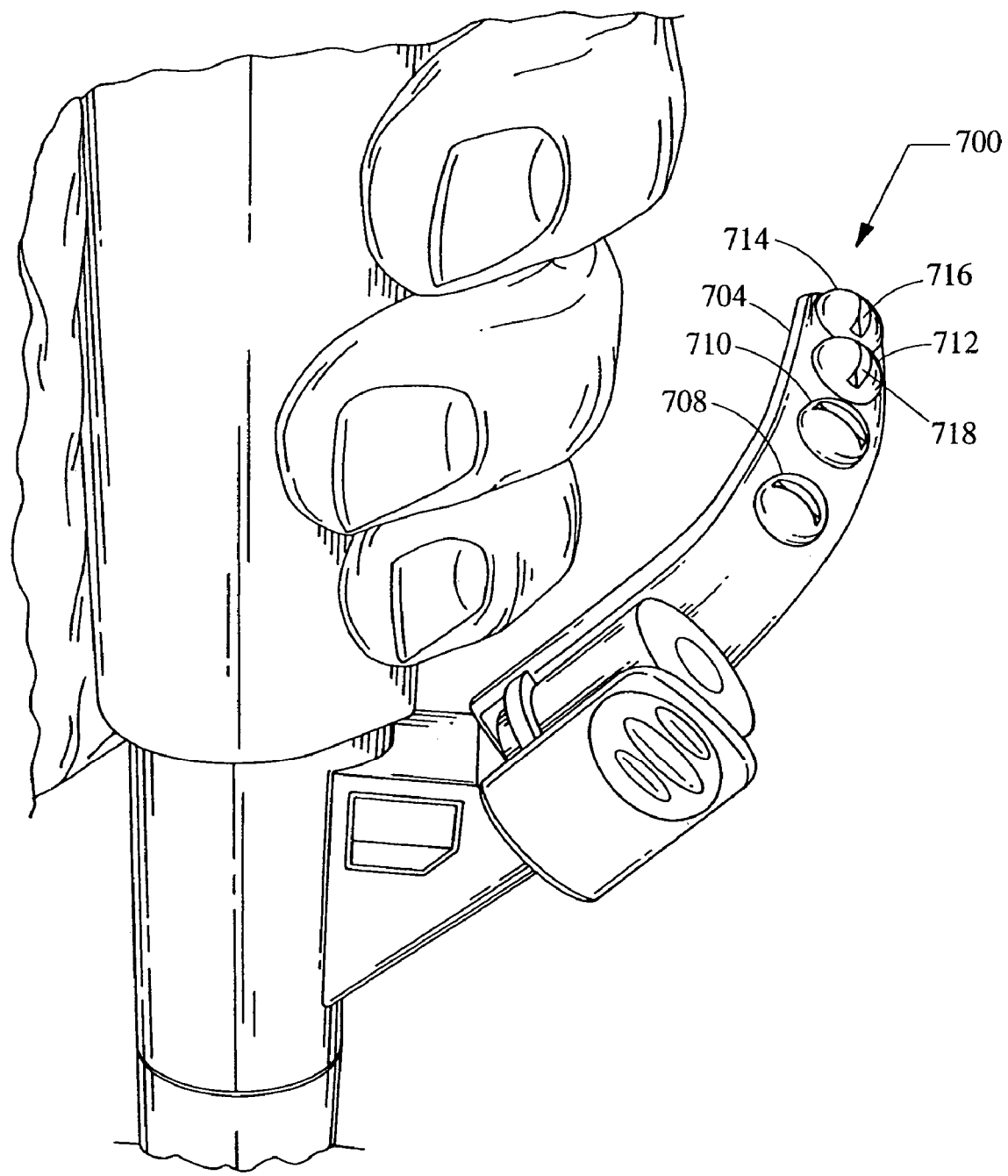
FIG. 7 illustrates an exemplary wire guide holder affixed to an endoscope.

FIG. 7 illustrates another exemplary embodiment of a wire guide holder 700 affixed to an endoscope 702. The wire guide holder 700 has a wire holder 704 and a seal holder 706. The wire holder 704 has securing T-shaped knobs 708, 710, 712 around which a wire guide may be weaved and secured. The securing knobs 708, 710, 712 may be arranged in a line so as to force a wire guide to weave between the knobs 708, 710, 712. The wire holder 704 also has a wire passageway 714, into which a wire guide may be received. This exemplary wire passageway 714 has an entry slot or opening 716 that is biased towards a closed position, and a receptacle area 718 that is biased in an open position. In this way, a wire guide may be woven between the knobs 708, 710, 712 and forced through the entry 716 into the receptacle area 718 of the wire passageway 714, where it may be retained. Alternatively, wire passageway 714 can be omitted, and the wire guide can be secured by simply weaving it laterally between knobs 708, 710, and 712.

Figure 8:
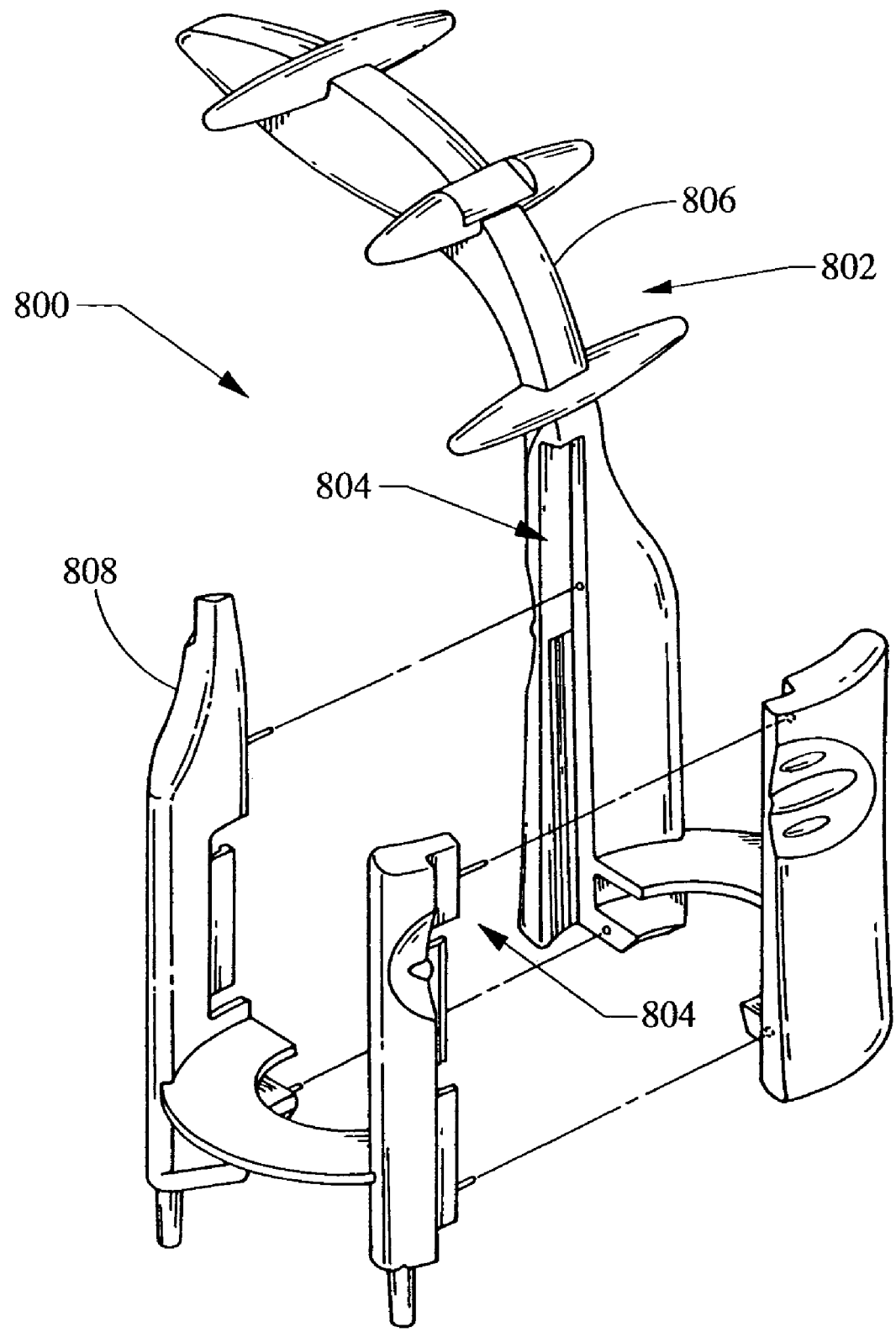
FIG. 8 illustrates a partial view of an exemplary disassembled snap-fit wire guide holder.

FIG. 8 illustrates an exemplary embodiment of a disassembled wire guide holder 800. The wire guide holder 800 has a wire holder 802 and a seal holder 804. This exemplary wire guide holder 800 is in two pieces 806, 808 formed of a suitable material such as plastic that may be snap-fit together around a seal (not shown). Although the exemplary embodiment illustrated here is constructed by two pieces snap-fit together, wire guide holders may be made of any of one or more pieces that may be affixed together in any way. For example, pieces may be ultrasonically bonded, heat bonded, glued together, or affixed in any other way.

Figure 9:
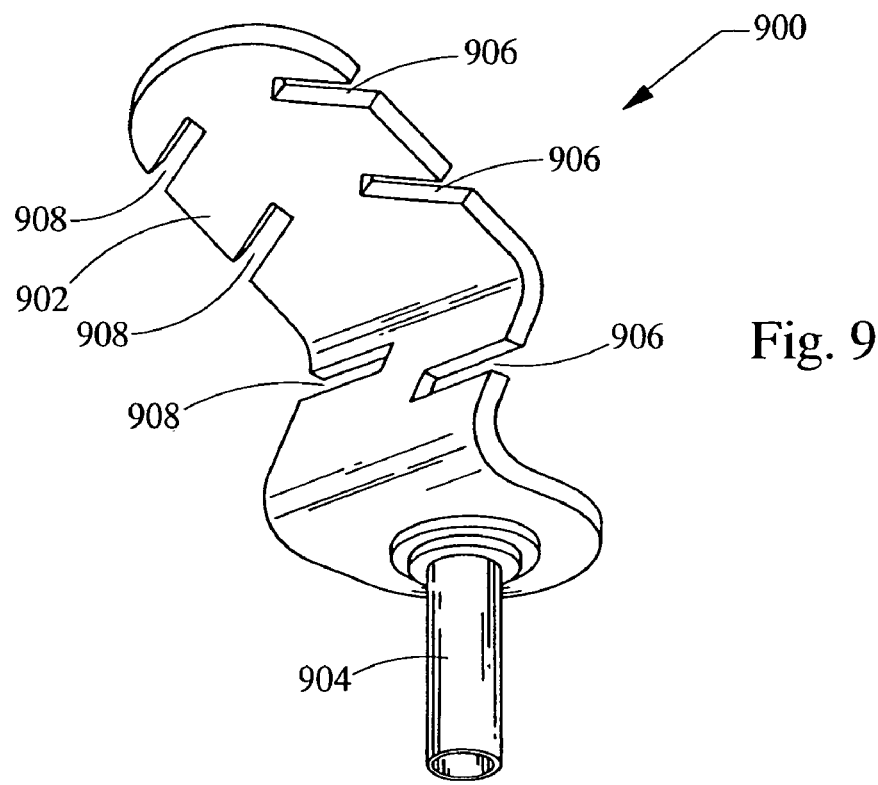
FIG. 9 illustrates an exemplary wire guide holder.

FIG. 9 illustrates another exemplary wire guide holder 900 having a wire holder 902 and an insertion portion 904. The wire holder 902 has two sets of three cut out sections 906, 908. A wire guide may be weaved between the cut outs to restrict movement of the wire guide. As noted with respect to previous embodiments, in this particular embodiment, two or more wire guides (or other elongate devices) can be secured by wire guide holder 900—one in each set of cut out sections 906, 908, respectively. Further, although three cut out sections are shown in each set of cut out sections, any number of cut out sections may be used. The insertion portion 904 may be inserted into an access port of an endoscope, for example, into the metal insert 202 shown in FIG. 2. Although not required, wire guide holder 900 can house a seal (not shown) within insertion portion 904. Such a seal can be used to limit the escape of fluids between the wire guide holder and the endoscope. Additionally, a second similar seal can be provided around the exterior of insertion portion 904, between insertion portion 904 and the endoscope working channel, to limit the escape of fluids from the working channel. Of course, as with the previously described embodiments, the use of a seal is not required.

Figure 10:
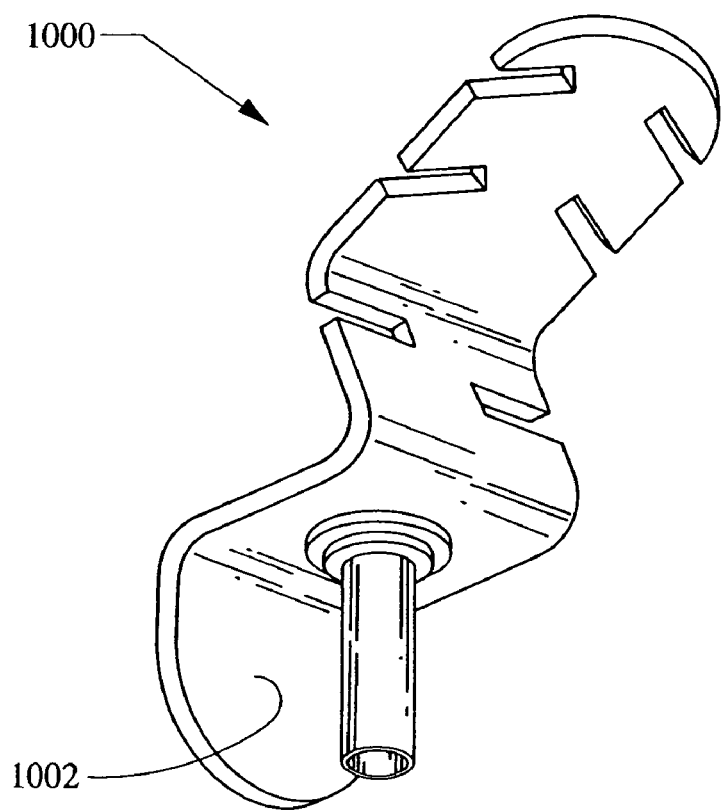
FIG. 10 illustrates an exemplary wire guide holder having a stabilizing lip.

FIG. 10 illustrates an exemplary wire guide holder 1000 similar to that shown in FIG. 9. This wire guide holder 1000 has a stabilizing lip 1002 that hangs over a part of an access port of an endoscope when the wire guide holder 1000 is engaged with the endoscope. The stabilizing lip 1002 can optionally provide a force against the access port of the endoscope to provide additional stability. Alternately, a doctor can press the stabilizing lip 1002 against the endoscope to provide additional stability for the wire guide holder 1000.

Figure 11:
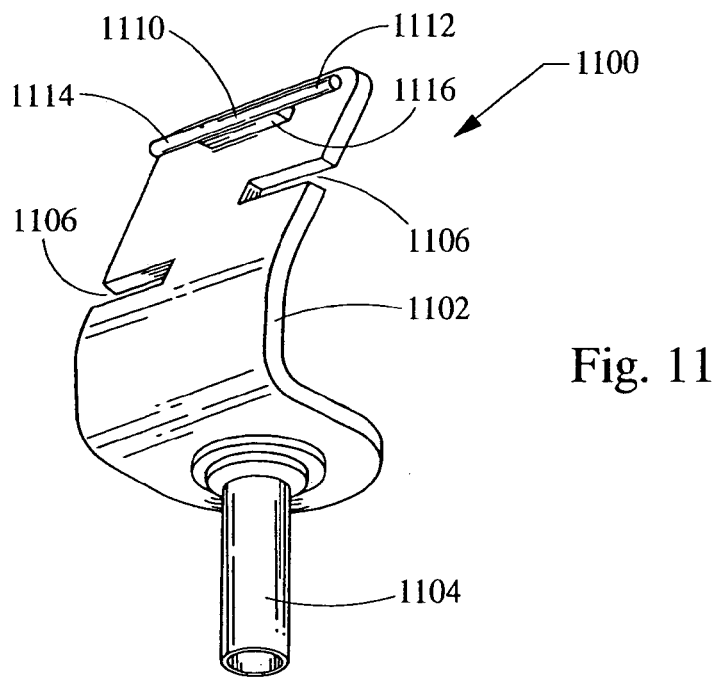
FIG. 11 illustrates an exemplary wire guide holder.

FIG. 11 illustrates an exemplary wire guide holder 1100, which engages an endoscope in a similar manner to the wire guide holder 900 of FIG. 9. This wire guide holder 1100 includes a wire holder 1102 and an insertion portion 1104. The wire holder 1102 includes two offsetting cut outs 1106, 1108, which can receive one or more wire guides, respectively. The wire holder 1102 also includes a receiving bar 1110 having two receiving protrusions 1112, 1114 and a central receiving base 1116. In use, a wire guide can be threaded through cut out 1106 and receiving protrusion 1112. Once in receiving protrusion 1112, a doctor has a number of options for disposition of the wire guide. For example, a doctor can leave the wire guide as is, bend the wire guide at an angle to the plane of the wire holder 1102, wrap the wire guide around the central receiving base 1116, pass the wire guide through receiving protrusion 1114, or perform some combination of these actions.

Figure 12:
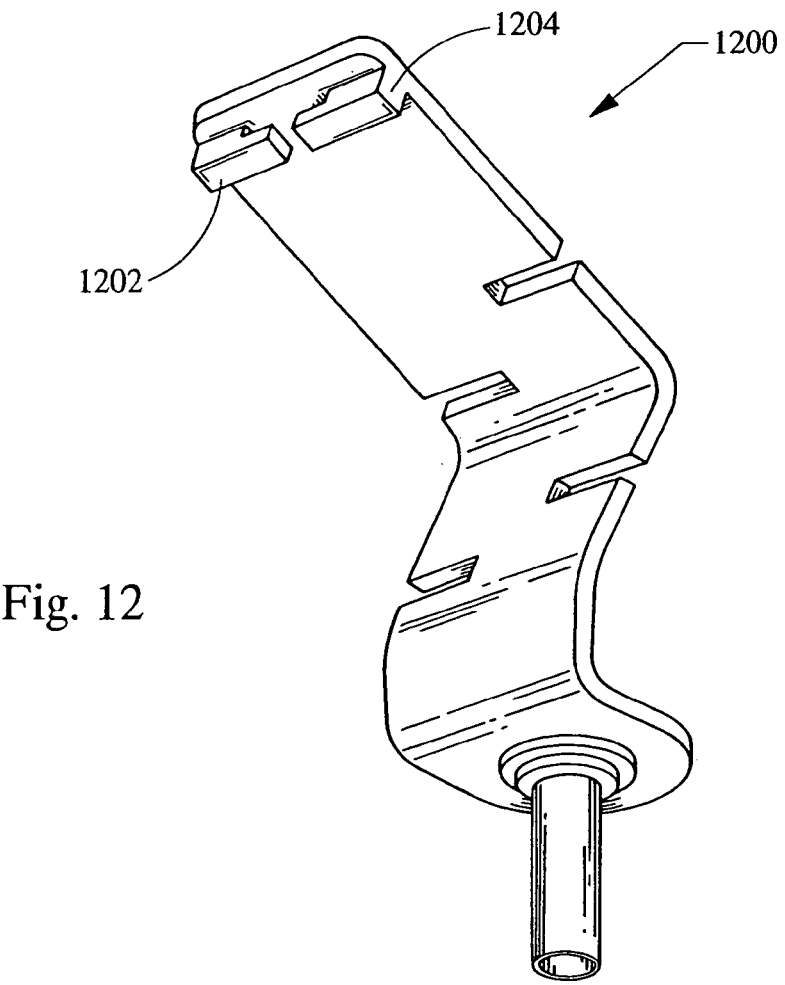
FIG. 12 illustrates an exemplary wire guide holder.

FIG. 12 illustrates an exemplary wire guide holder 1200 similar to that of FIG. 11. This wire guide holder has a pair of receiving arms 1202, 1204, which receives one or more wire guides, respectively. These arms 1202, 1204 can be used in a similar manner as the receiving protrusions 1112, 1114 of FIG. 11.

FIG. 13 illustrates an exemplary wire guide holder 1300 having a wire holder 1302 and an insertion portion 1304. The wire holder 1302 includes two sets of cut outs 1306, 1308 that may receive at least two wire guides, respectively, and a common entry slot 1312 and receiving slot 1310. In use, a wire guide may be threaded through one set of cut outs 1306, through the entry slot 1312 and into the receiving slot 1310.

FIG. 14 illustrates an exemplary wire guide holder 1400 similar to the wire guide holder 1100 of FIG. 11. This wire guide holder 1400 includes a wire holder 1402 and an insertion portion 1404. The wire holder 1402 includes two offsetting cut outs 1406, 1408 that may receive at least two wire guides, respectively. The wire holder 1402 also includes a protruding, central receiving base 1410. The central receiving base 1410 may separate multiple wire guides threaded through cut outs 1406, 1408, respectively.

Figure 15:
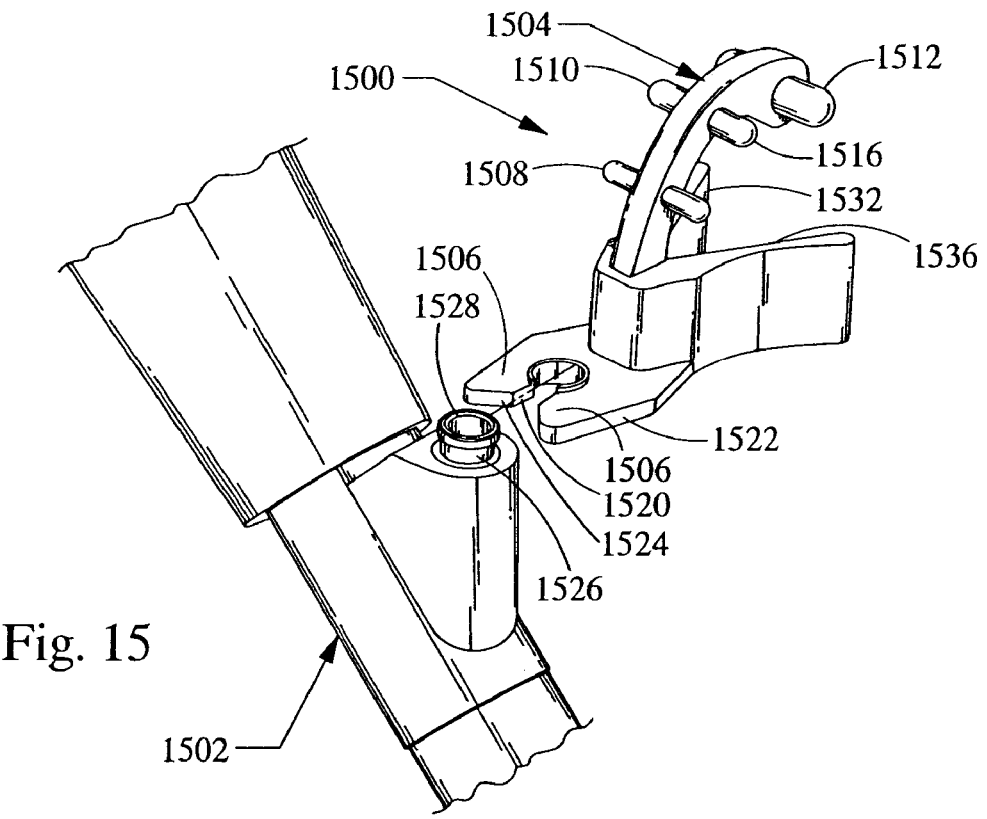
FIG. 15 illustrates an exemplary wire guide holder and endoscope.

FIG. 15 illustrates an exemplary wire guide holder 1500 and endoscope 1502. The wire guide holder has a wire holder 1504 and an engagement portion 1506. The wire holder 1504 has three securing posts 1508, 1510, 1512, having three guide grooves 1514 (not shown), 1516 and 1518 (not shown), respectively. In this example, the securing posts 1508, 1510, 1512 increase in circumference. The engagement portion 1506 has two engagement clamps 1520, 1522 forming a circular beveled edge 1524. The beveled edge 1524 engages a metal insert 1526 of an access port 1528 of an endoscope 1502. Further, the engagement portion 1506 includes two finger presses 1530, 1532 that may be pushed towards one another to flex the engagement portion 1506 and separate the clamps 1520, 1522.

Figure 16:
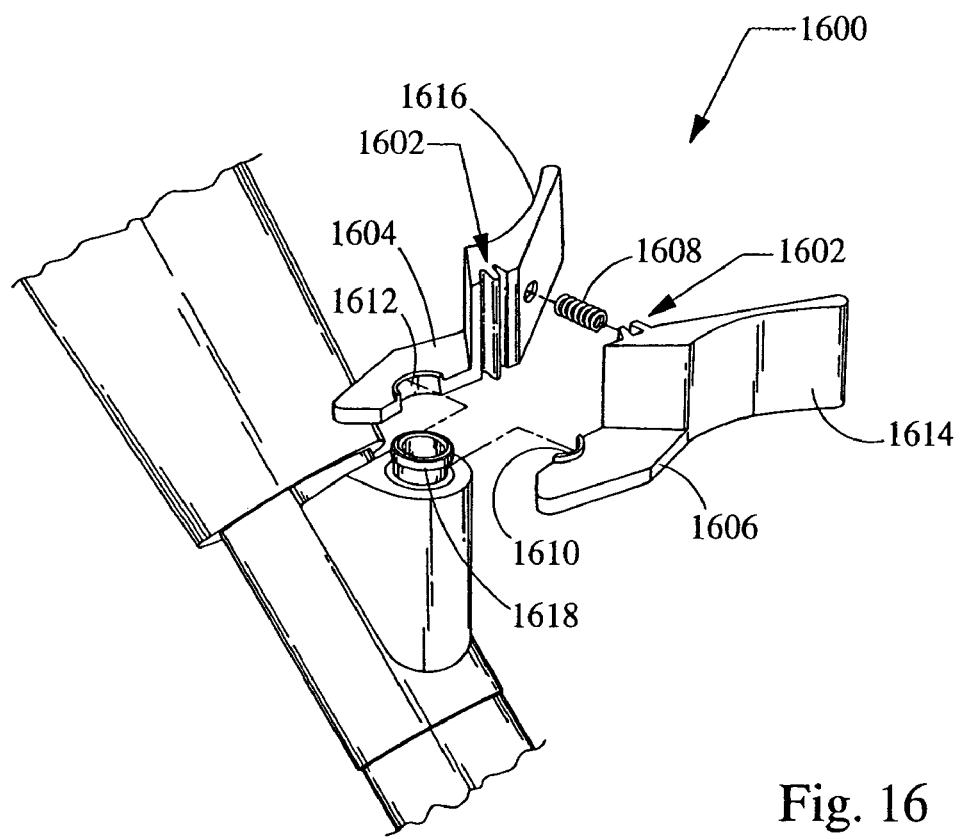
FIG. 16 illustrates an exemplary wire guide holder and endoscope.

FIG. 16 illustrates an alternate engagement portion 1600 that may be used together with the wire holder 1504 of wire guide holder 1500 of FIG. 15. This engagement portion 1600 can alternatively be used with any other wire holder illustrated herein or suitable for use with a scope. Indeed, as will become apparent to one of ordinary skill, many of the features described and illustrated herein regarding a particular embodiment can be combined with other embodiments described and illustrated herein. The engagement portion 1600 includes a pivot hinge 1602 between the two halves 1604, 1606 of the engagement portion 1600 and a return spring 1608. Each half 1604, 1606 includes an engagement clamp 1610, 1612 and finger press 1614, 1616, respectively. When the finger presses 1614, 1616 are pushed towards one another, the return spring 1608 is compressed and the engagement clamps 1610, 1612 are separated about the pivot hinge 1602. The clamps 1610, 1612 may then be moved into or out of engagement with a metal insert 1618 of an access port 1620 of an endoscope 1622. Once the engagement portion 1600 is moved into position about the metal insert 1618, the finger presses 1614, 1616 may be released to close the clamps 1610, 1612 about the metal insert 1618.

Figure 17:
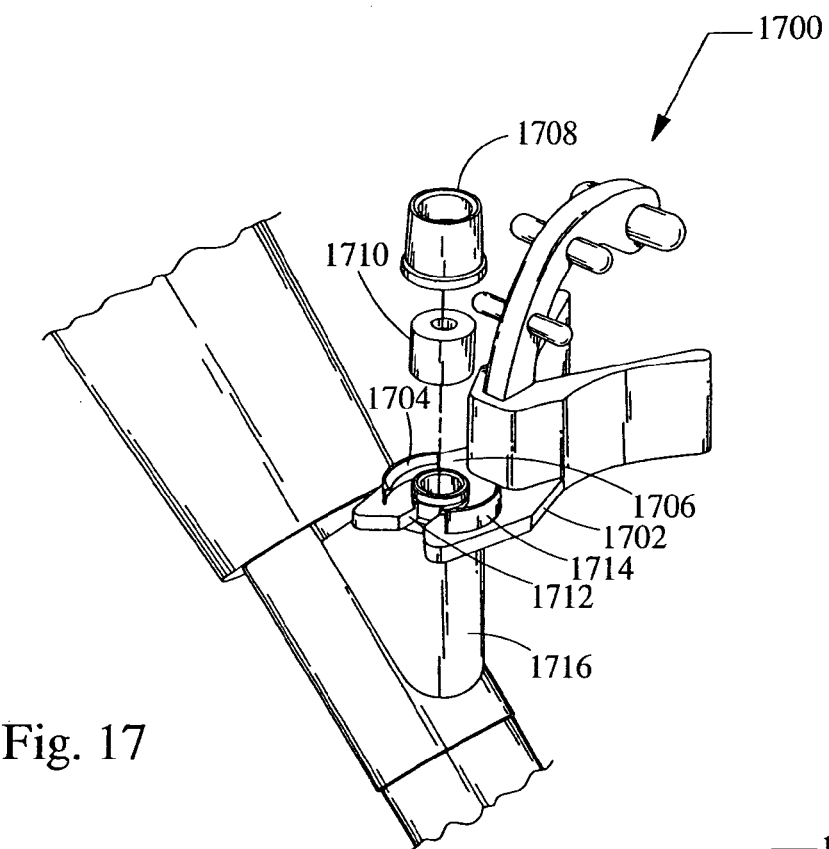
FIG. 17 illustrates an exemplary wire guide holder, rubber seal, snap-fit cap, and endoscope.

FIG. 17 illustrates an exemplary wire guide holder 1700 that includes a cap snap 1702 having a beveled edge 1704 and receiving notch 1706. Snap-fit cap 1708 is designed to fit about a rubber seal 1710 and into the beveled edge 1704 and receiving notch 1706. That is, the rim provided around snap-fit cap 1708 snaps into receiving notch 1706. This wire guide holder 1700 is similar in appearance and operation to the wire guide holder 1500 of FIG. 15. However, this wire guide holder 1700 may allow doctors to use different types of rubber seals with a single wire guide holder. In use, the wire guide holder 1700 may be engaged about a metal insert 1712 of an access port 1714 of an endoscope 1716. Then, the desired rubber seal 1710 may be placed over the metal insert 1712. Finally, the rubber seal 1710 is secured against the metal insert 1712 by the snap-fit cap 1708.

Figure 18:
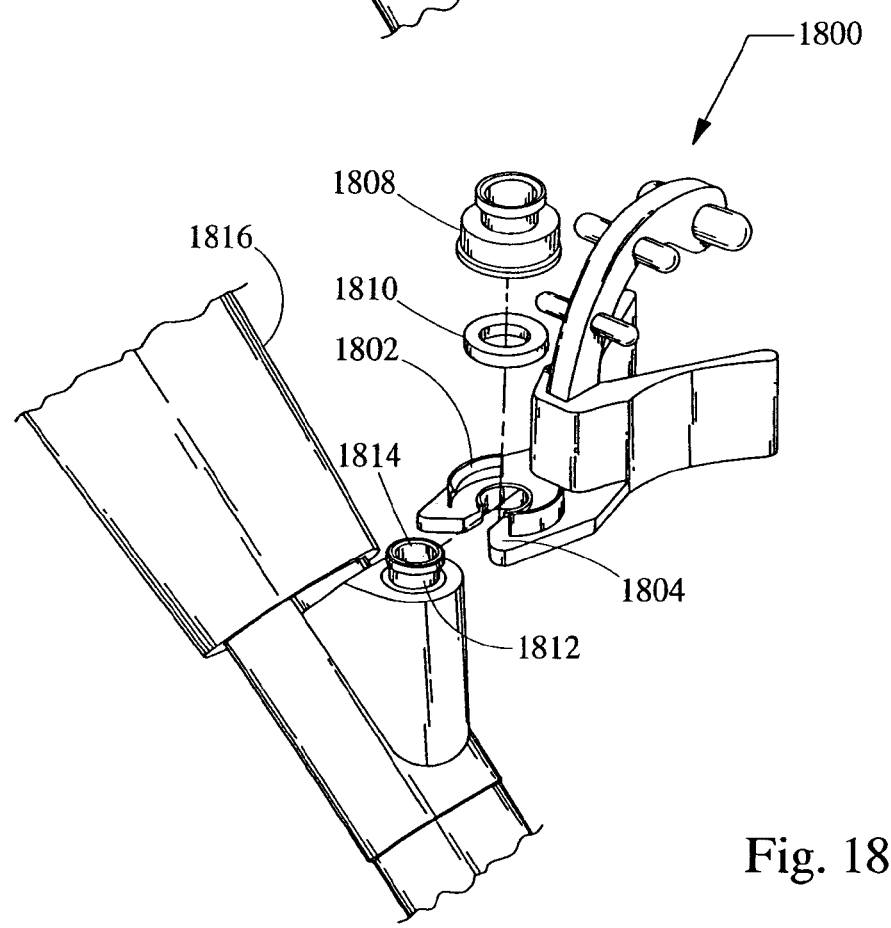
FIG. 18 illustrates an exemplary wire guide holder, rubber gasket, replica of channel insert, and endoscope.
Figure 19:
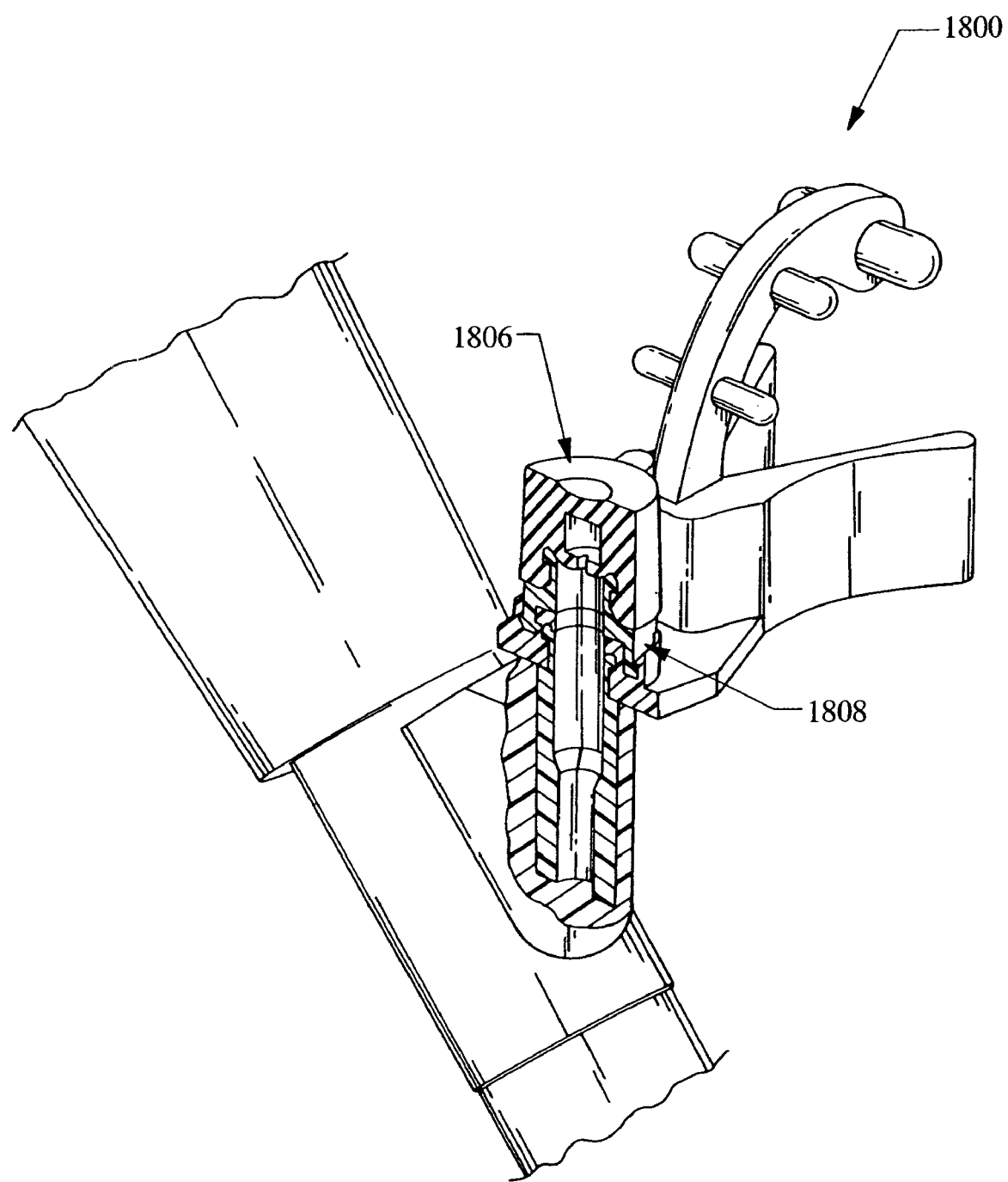
FIG. 19 illustrates a cut away view of the exemplary wire guide holder of FIG. 18 and a seal.

FIG. 18 illustrates an exemplary wire guide holder 1800 similar to that of FIG. 17, having a beveled edge 1802 and receiving notch 1804 adapted to receive the rim around 1808. This wire guide holder 1800 may allow a doctor to use a seal (not shown) designed to be fitted over the metal insert with the wire guide holder 1800. The wire guide holder 1800 provides an insert channel rim replica 1808 adapted to receive the seal, and a rubber gasket 1810. After placement of the wire guide holder 1800, the rubber gasket 1810 may be fitted over a metal insert 1812 of an access port 1814 of an endoscope 1816. The insert channel rim replica 1808 may then be fitted over the rubber gasket 1810 and secured in the beveled edge 1802 and receiving notch 1804. FIG. 19 illustrates a cut away view of the exemplary wire guide holder 1800, seal 1806, insert channel rim replica 1808, and rubber gasket 1810.

Figure 20:
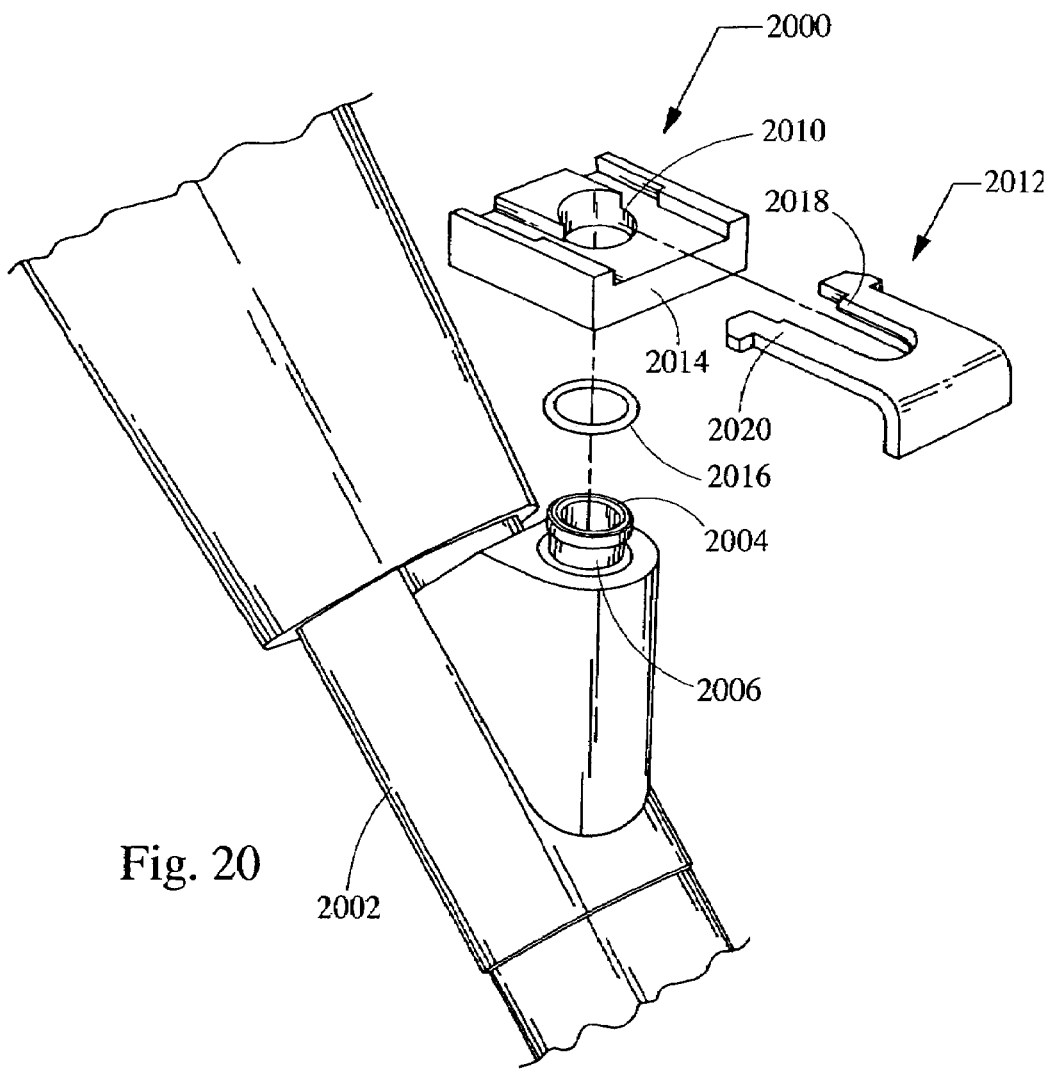
FIG. 20 illustrates an exploded view of an exemplary securing mechanism and endoscope.

FIG. 20 illustrates an exemplary engagement portion 2000 and an endoscope 2002 having an access port 2004 with a metal insert rim 2006 and metal insert groove 2008. The engagement portion 2000 includes a base 2010 that has a slot 2014 to receive a wedge slide 2012 and that has a rubber o-ring 2016 to seal the base 2010 to the metal insert rim 2006. The wedge slide 2012 has ramped surfaces 2018, 2020 that engage the metal insert groove 2008 when in use. The engagement portion 2000 may be used with a variety of wire holders, seals, and other devices that engage the access port 2004 of an endoscope 2002.

Figure 21:
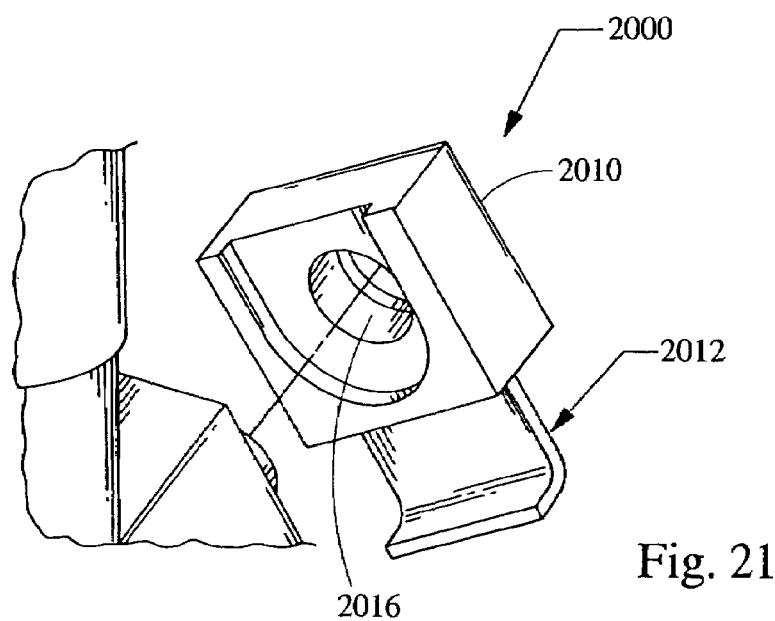
FIG. 21 illustrates a bottom view of the exemplary securing mechanism and endoscope of FIG. 20.
Figure 22:
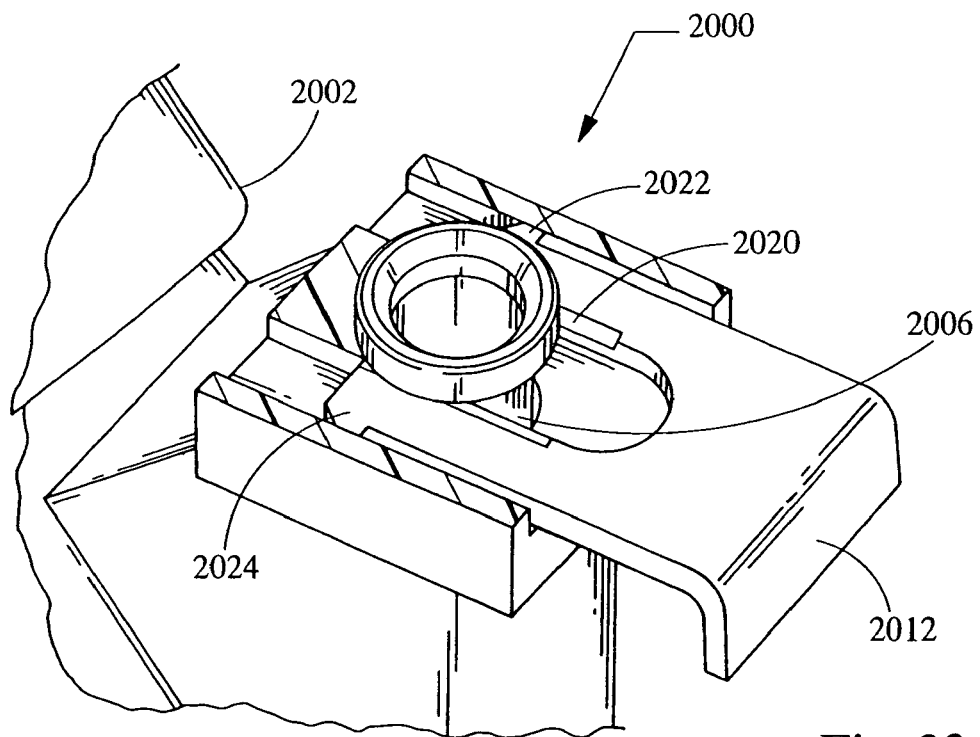
FIG. 22 illustrates a cut away view of the exemplary securing mechanism and endoscope of FIG. 20.
Figure 23:
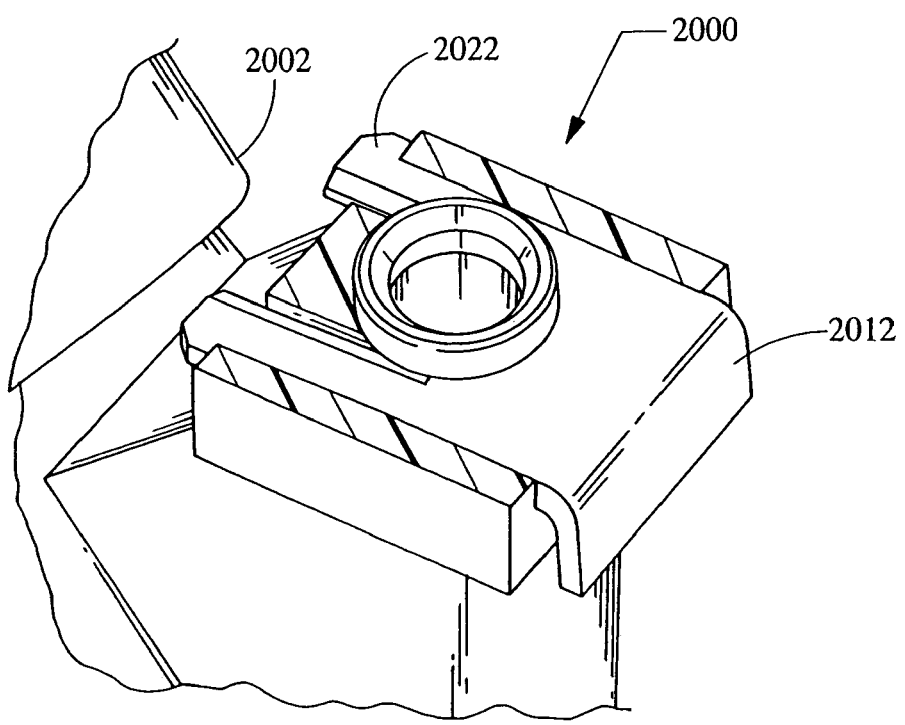
FIG. 23 illustrates a cut away view of the exemplary securing mechanism and endoscope of FIG. 20.
Figure 24A:
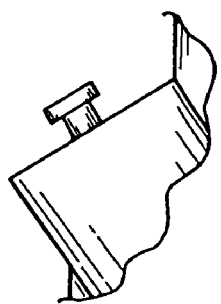
FIG. 24 illustrates an exemplary securing mechanism.
Figure 24B:
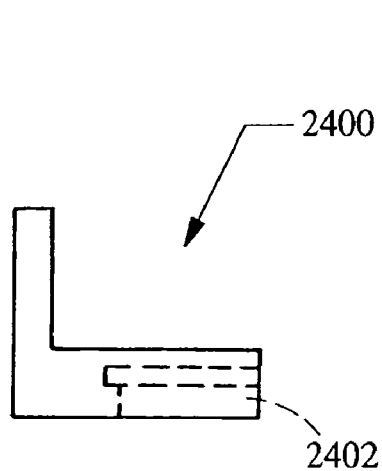
Figure 24C:
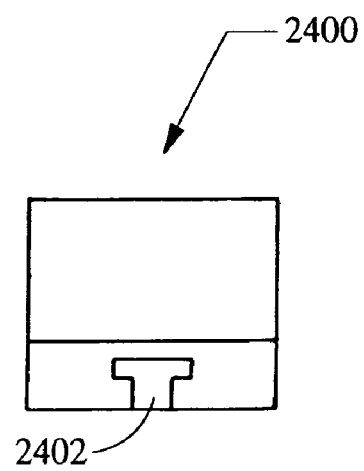
Figure 24D:
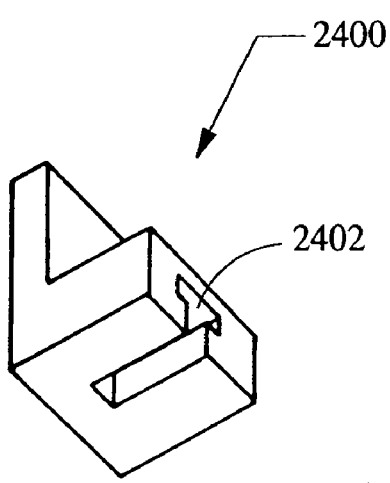
Figure 24E:
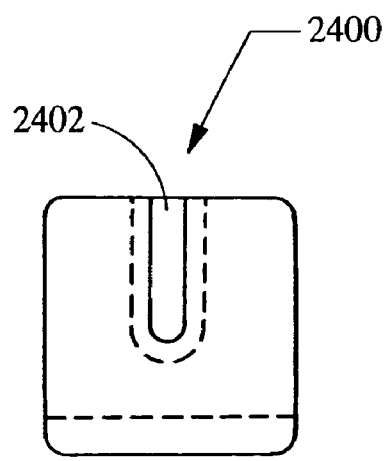

FIG. 21 illustrates the engagement portion 2000 with the wedge slide 2012 inside the base 2010 and the rubber o-ring 2016 in position against a flange or counter-bore in the underside of the base 2010. Also illustrated are tabs 2022, 2024 (best shown in FIG. 23) that are configured to engage the ends of the base 2010. FIG. 22 illustrates the engagement portion 2000 fitted about the metal insert rim 2006, with the top of the engagement portion 2000 removed for clarity. In FIG. 22, the ramped surfaces 2018, 2020 of the wedge slide 2012 are about to engage the metal insert groove 2008 to secure the engagement portion 2000 to the endoscope 2002. FIG. 23 illustrates the engagement portion 2000 secured to the endoscope 2002, with the wedge slide 2012 engaged about the metal insert groove 2008 and the ends of the wedge slide 2012 engaged with the tabs 2022, 2024.

FIGS. 24*a-e* illustrate an exemplary securing mechanism 2400 for engagement with a lip of an insert of an access port of an endoscope (not shown). The securing mechanism 2400 has a groove 2402 that is fitted to the lip of the insert. The securing mechanism 2400 may be slid over the lip, with the lip retaining the fitted groove 2402 and holding the securing mechanism 2400 in place.

Figure 25:
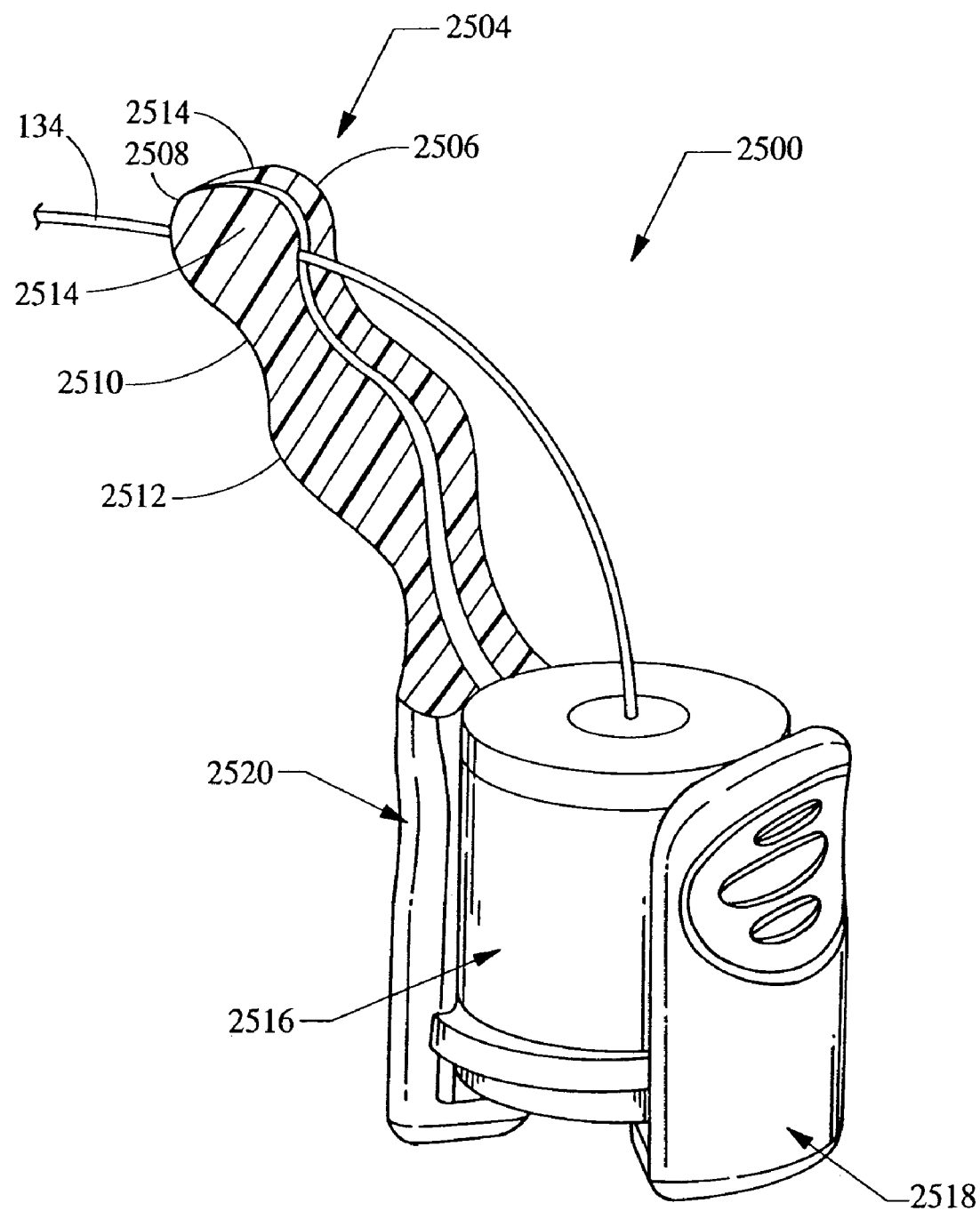
FIG. 25 illustrates an exemplary securing mechanism.

FIG. 25 illustrates an exemplary wire guide holder 2500. Wire guide holder 2500 is similar to the previously described wire guide holders. As illustrated in FIG. 25, however, wire guide holder 2500 has a wire holder 2504 configured to secure wire guide 134 in a "clothspin" style arrangement. In particular, opposing stems 2506 and 2508 form a natural fulcrum about neck 2510. Squeezing finger presses 2512, which are formed on stems 2506 and 2508 below neck 2510, causes upper portions 2514 to separate, thus allowing the wire guide to be either inserted or released from wire holder 2504. In addition, as discussed with respect to the previous embodiments, finger presses 2518 and 2520 are provided for engaging the and disengaging the wire guide holder 2500 and the endoscope. A seal 2516 is also optionally provided to limit the escape of fluids from the working channel of the endoscope.

Figure 26:
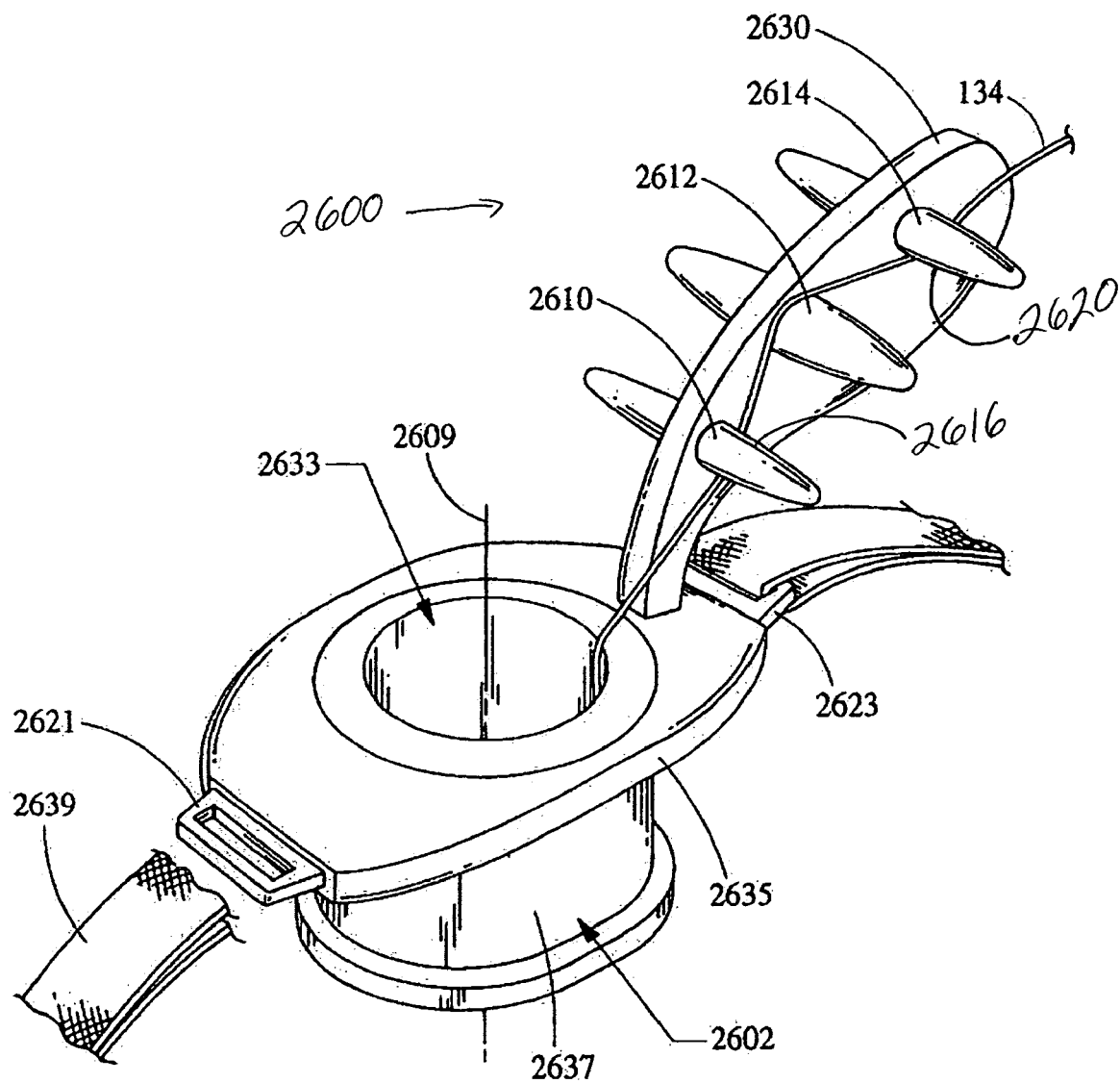
FIG. 26 illustrates a perspective view of an exemplary bite block wire guide holder.

As illustrated in FIGS. 26-29, a wire guide holder can be configured to secure a wire guide to a bite block. In general, FIG. 26 illustrates a wire guide holder 2600 having a central neck or spine 2630. Central spine 2630 extends and curves away from the central or vertical axis 2609 formed by bite block 2602. Central spine 2630 can be pivotally or rigidly attached to bite block 2602. Three spaced apart posts 2610, 2612, 2614, extend generally perpendicularly from central spine 2630. Each post includes a guide groove. In particular, post 2612 includes a single, relatively large guide groove 2618 that extends over an upper portion of central spine 2630. Posts 2610 and 2614 define guide grooves 2616 and 2620, respectively, located on a lower portion of the posts. Each guide groove defines a gap having a width that is greater than the width of a typical wire guide or elongate medical device 134.

Figure 27:
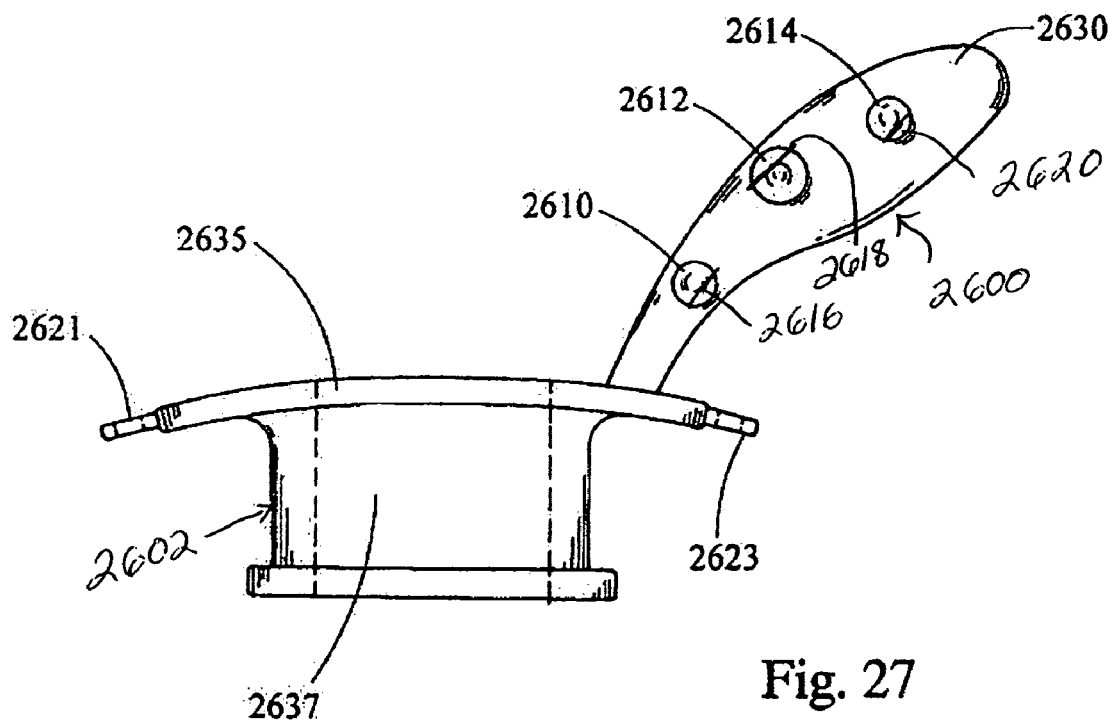
FIG. 27 illustrates a side view of an exemplary bite block wire guide holder.
Figure 28:
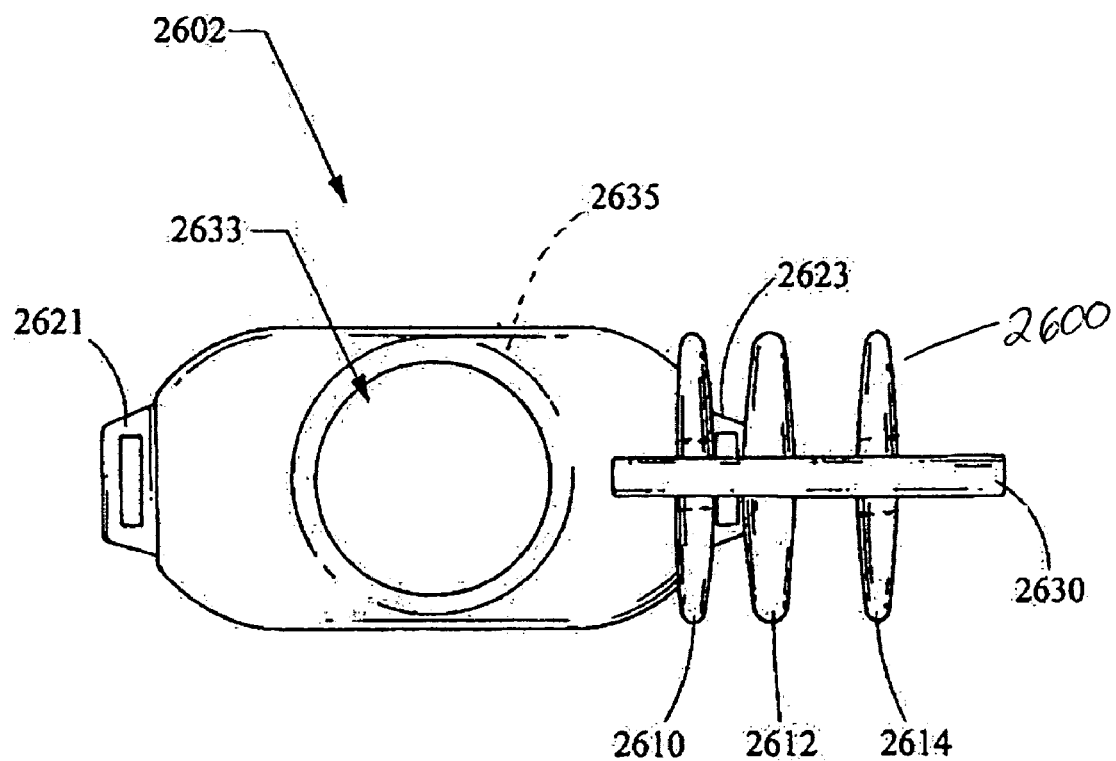
FIG. 28 illustrates a top view of an exemplary bite block wire guide holder.

As illustrated in FIGS. 26-28, central spine 2630 is attached to a bite block 2602. In general, a bite block prevents a patient from inadvertently biting down on medical instruments in the patient's mouth. Biting down on a medical instrument can result in the patient injuring him or herself, or damaging a medical instrument.

As illustrated in FIGS. 26-29, bite block 2602 includes bite rim 2637, retention lip 2635, insertion passageway 2633, and strap slots 2621. Bite block 2602 can be provided in a variety of sizes. This allows a physician to use medical instruments of varying sizes. Typically, the diameter of bite block insertion passageway is 15 mm or less. However, the diameter of the insertion passageway 2633 can be equal to or greater than 22 mm. An enlarged bite block diameter allows a physician to pass relatively large instruments or devices through the esophagus. Bite block 2602 is formed of a rigid plastic or other material. Bite rim 2637 is inserted into the patient's mouth. Retention lip 2635 and retaining strap 2639 (FIG. 29) secure the bite block to the patient's mouth and prevent the patient from inadvertently swallowing, choking on, or expelling the bite block.

Figure 29:
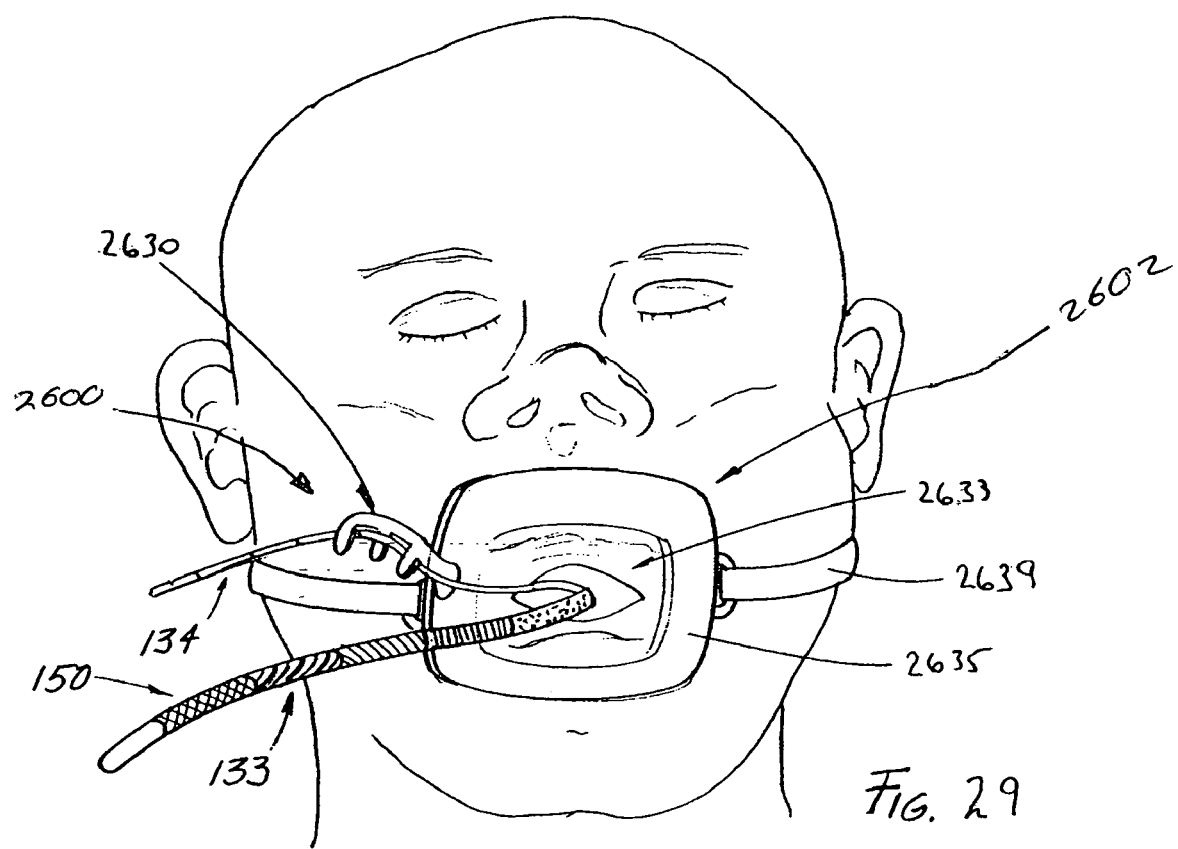
FIG. 29 illustrates a top view of an exemplary bite block wire guide holder strapped to a patient's head.

Wire guide holder 2600 is configured for use in a variety of medical procedures in which a wire guide is used in the upper gastrointestinal tract. For example, wire guide holder 2600 can be used in procedures requiring esophageal dilation to stretch or open a blocked portion of the esophagus. For use in an esophageal dilation, bite block 2602 is first secured to the patient's mouth with retaining strap 2639, as illustrated in FIG. 29. Once the bite block is in place, an endoscope is passed through the insertion passageway 2633 and advanced through the esophagus to the site of the stricture. A wire guide is then inserted through the working channel of the endoscope and advanced across the stricture. The endoscope is then removed while maintaining the position of the wire guide relative to the stricture.

After the endoscope is removed, a physician can weave the proximal end of wire guide 134 between posts 2610, 2612, and 2614, as shown in FIG. 26. Preferably, about 10 cm of the wire guide extends beyond wire guide holder 2600. As discussed above, when wire guide 134 is weaved around the securing posts, the wire guide is restricted against longitudinal movement. Once the wire guide is secured to the bite block (and relative to the stricture), the physician can freely load a lead catheter over the proximal end of the wire guide. When the lead catheter is loaded over the wire guide, the physician typically releases the wire guide from the wire guide holder so as to advance the lead catheter past the wire guide holder. At this point, the physician can re-secure the wire guide to the wire guide holder as discussed above. The lead catheter can now be easily advanced along the wire guide's path through the esophagus to the site of the stricture to perform the esophageal dilation. After the esophageal dilation, the lead catheter is pulled proximally over the wire guide to a position distal to the wire guide holder, the wire guide is released, and the catheter can be removed from the patient. Alternatively, the lead catheter can be intra-luminally advanced beyond the distal end of the wire guide so as to release the lead catheter from the wire guide. Such an intra-luminal exchange allows the lead catheter to be completely withdrawn from the patient while maintaining the position of the wire guide. In some cases, it may be necessary to repeat this procedure with larger lead catheters to more fully dilate an esophageal stricture.

Wire guide holder 2600 can also be used in percutaneous esophageal gastrostomy (PEG) tube placement. First, an esophagogastroduodenoscopy (EGD) is performed according to well-known practice. A small incision is then made in the patient's abdomen and a needle is inserted into the insufflated stomach. A short wire guide (typically less than 100 cm) is passed through the needle and into the stomach. A snare is then passed through the working channel of the endoscope to the location of the wire guide. The snare is used to grasp and retract the wire guide out of the esophagus and the patient's mouth. Approximately 10 cm of the wire guide should protrude from the patient's mouth. At this point in the procedure, the proximal portion of the wire guide (relative to the patient's mouth) can be secured to the wire guide holder as described above. A PEG lead catheter is then loaded onto the wire guide. Subsequently, the wire guide is released from the wire guide holder, the PEG lead catheter is passed into the mouth, and the wire guide is re-secured to the wire guide holder. The PEG lead catheter can then be guided over the secured wire guide using conventional PEG tube placement techniques. Once the PEG tube is in place, the wire guide is released and withdrawn according to standard procedures.

Novel features of the disclosed wire guide holder can be successfully used in a variety of applications. Indeed, the wire guide holder device disclosed herein can be used in a vast number of widely differing medical procedures. In particular, the disclosed wire guide holder can be used in medical procedures in which one or more elongate medical instruments such as a catheter or guide wire needs to be secured relative to either a patient or another medical instrument. Exemplary procedures of this sort are further disclosed and discussed in Application Ser. No. 60/491,408, filed Jul. 31, 2003, Application Ser. No. 60/563,968, filed Apr. 21, 2004, Application Ser. No. 60/565,030, filed Apr. 23, 2004, and Application Ser. No. 60/571,142, filed May 14, 2004, each of which is incorporated herein by reference.

Any other undisclosed or incidental details of the construction or composition of the various elements of the disclosed embodiment of the present invention are not believed to be critical to the achievement of the advantages of the present invention, so long as the elements possess the attributes needed for them to perform as disclosed. The selection of these and other details of construction are believed to be well within the ability of one of even rudimentary skills in this area in view of the present disclosure. Illustrative embodiments of the present invention have been described in considerable detail for the purpose of disclosing a practical, operative structure whereby the invention may be practiced advantageously. The designs described herein are intended to be exemplary only. The novel characteristics of the invention may be incorporated in other structural forms without departing from the spirit and scope of the invention. Indeed, different features of the disclosed embodiments can be integrated into a single structure, or alternatively, provided as separate pieces. For example, the clamp portion of the disclosed embodiments can be provided separate from the wire holder portion. Also, as discussed above, seals can also be provided separately, or omitted altogether, from the previously described embodiments.

Unless otherwise indicated, all ordinary words and terms used herein shall take their customary meaning as defined in The New Shorter Oxford English Dictionary, 1993 edition. All technical terms shall take on their customary meaning as established by the appropriate technical discipline utilized by those normally skilled in that particular art area. All medical terms shall take their meaning as defined by Stedman's Medical Dictionary, 27th edition.

The invention claimed is:

1. A wire guide holder for securing an elongate medical device relative to a second medical device, the wire guide holder comprising:
   a spine; and
   a plurality of projections extending outwardly from the spine,
   wherein the elongate medical device is woven through the plurality of projections to thereby secure the elongate medical device against axial movement relative to the second medical device, the plurality of projections configured to frictionally engage opposing sides of the elongate medical device at spaced apart locations and guide the elongate medical device along a non-linear pathway,
   wherein the second medical device is an elongate medical tube, and
   wherein the wire guide holder further comprises:
   a body connected to the spine, the body having an attachment portion configured for attachment to the elongate medical tube;
   and a seal supported by the body, wherein the seal comprises a rubber housing and a foam disk disposed within the rubber housing, the seal having a passageway therethrough, wherein the passageway is configured to sealingly receive the elongate medical device.

2. The wire guide holder of claim 1, wherein the elongate medical tube is an endoscope.

3. The wire guide holder of claim 1, wherein the elongate medical tube is a catheter.

4. The wire guide holder of claim 2 wherein the endoscope includes an access port, and the attachment portion of the body is configured for attachment to the access port.

5. The wire guide holder of claim 4, wherein the access port includes an insert, and the attachment portion is configured for attachment to the insert.

6. The wire guide holder of claim 5, wherein the attachment portion comprises a wedge slide configured to secure the body to the insert.

7. The wire guide holder of claim 1 wherein the attachment portion further comprises a clamp, the clamp being configured to clamp the body to the elongate medical tube.

8. The wire guide holder of claim 1 wherein the body is fixedly connected to the elongate medical tube.

9. A system for holding a wire guide comprising:
   an endoscope having an access port including an insert disposed therein, the insert having a groove; and
   a wire guide holder affixed to the insert, the wire guide holder configured to secure an elongate member against axial movement relative to the endoscope by frictionally engaging opposing sides of the elongate member at spaced apart locations and guide the elongate member along a non-linear pathway,
   wherein the wire guide holder is disposed within the groove and is clamped to the insert.

10. The system of claim 9, wherein the insert has a rim and wherein the wire guide holder is clamped to the rim.

11. The wire guide holder of claim 1, wherein each of the plurality of projections are configured to engage one side of the elongate medical device.

12. The wire guide holder of claim 1, wherein the plurality of projections comprises at least three spaced apart projections.

13. The wire guide holder of claim 1, wherein the plurality of projections are configured to induce an S-shaped bend in the elongate medical device when the elongate medical device is woven therebetween.

* * * * *

UNITED STATES PATENT AND TRADEMARK OFFICE
CERTIFICATE OF CORRECTION

PATENT NO. : 7,637,863 B2 Page 1 of 1
APPLICATION NO. : 10/903679
DATED : December 29, 2009
INVENTOR(S) : Deal et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1331 days.

Signed and Sealed this

Ninth Day of November, 2010

David J. Kappos
*Director of the United States Patent and Trademark Office*